(12) United States Patent
Saito et al.

(10) Patent No.: US 11,862,662 B2
(45) Date of Patent: Jan. 2, 2024

(54) IMAGE DEVICE

(71) Applicant: Sony Semiconductor Solutions Corporation, Kanagawa (JP)

(72) Inventors: Sotetsu Saito, Kanagawa (JP); Suguru Saito, Kanagawa (JP); Nobutoshi Fujii, Kanagawa (JP)

(73) Assignee: Sony Semiconductor Solutions Corporation, Kanagawa (JP)

(*) Notice: Subject to any disclaimer, the term of this patent is extended or adjusted under 35 U.S.C. 154(b) by 453 days.

(21) Appl. No.: 17/279,352

(22) PCT Filed: Oct. 9, 2019

(86) PCT No.: PCT/JP2019/039744
§ 371 (c)(1),
(2) Date: Mar. 24, 2021

(87) PCT Pub. No.: WO2020/090384
PCT Pub. Date: May 7, 2020

(65) Prior Publication Data
US 2021/0408092 A1 Dec. 30, 2021

(30) Foreign Application Priority Data

Oct. 29, 2018 (JP) ................. 2018-202769

(51) Int. Cl.
*H01L 27/146* (2006.01)
(52) U.S. Cl.
CPC .... *H01L 27/1469* (2013.01); *H01L 27/14634* (2013.01); *H01L 27/14636* (2013.01)
(58) Field of Classification Search
CPC ......... H01L 27/14632; H01L 27/14634; H01L 27/14687; H01L 27/1469; H01L 21/304
See application file for complete search history.

(56) References Cited

U.S. PATENT DOCUMENTS

| 2010/0167445 | A1 | 7/2010 | Lee |
| 2014/0268609 | A1 | 9/2014 | Chien et al. |
| 2018/0040655 | A1* | 2/2018 | Nakashikiryo ... H01L 27/14683 |

FOREIGN PATENT DOCUMENTS

| JP | H09-106968 | 4/1997 |
| JP | 2013-214616 | 10/2013 |

(Continued)

OTHER PUBLICATIONS

International Search Report issued in International Patent Application No. PCT/JP2019/039744 dated Dec. 17, 2019 and English translation of same. 6 pages.

(Continued)

*Primary Examiner* — Robert G Bachner
*Assistant Examiner* — Molly K Reida
(74) *Attorney, Agent, or Firm* — K&L Gates LLP

(57) ABSTRACT

Provided is an imaging device (1) including: an imaging element (10); and a semiconductor element (20, 30) provided to be opposed to the imaging element and electrically coupled to the imaging element. The semiconductor element includes: a wiring region (20A, 30A) provided in a middle portion and a peripheral region (20B, 30B) outside the wiring region; a wiring layer (22, 32) having a wiring line in the wiring region; a semiconductor substrate (21, 31) opposed to the imaging element with the wiring layer interposed therebetween and having a first surface (Sa, Sc) and a second surface (Sb, Sd) in order from a side of the wiring layer; and a polishing adjustment section (23, 33) including a material that is lower in polishing rate than a constituent material of the semiconductor substrate, the polishing adjustment section being disposed in at least a portion of the peripheral region and provided in a thickness direction of the semiconductor substrate from the second surface.

10 Claims, 18 Drawing Sheets

(56) References Cited

FOREIGN PATENT DOCUMENTS

| | | |
|---|---|---|
| JP | 2014-099582 | 5/2014 |
| JP | 2016-058655 | 4/2016 |
| TW | 201314878 A | 4/2013 |
| TW | 201445713 A | 12/2014 |
| TW | 201705459 A | 2/2017 |
| TW | 201838096 A | 10/2018 |

OTHER PUBLICATIONS

Written Opinion issued in International Patent Application No. PCT/JP2019/039744 dated Dec. 17, 2019. 3 pages.

* cited by examiner

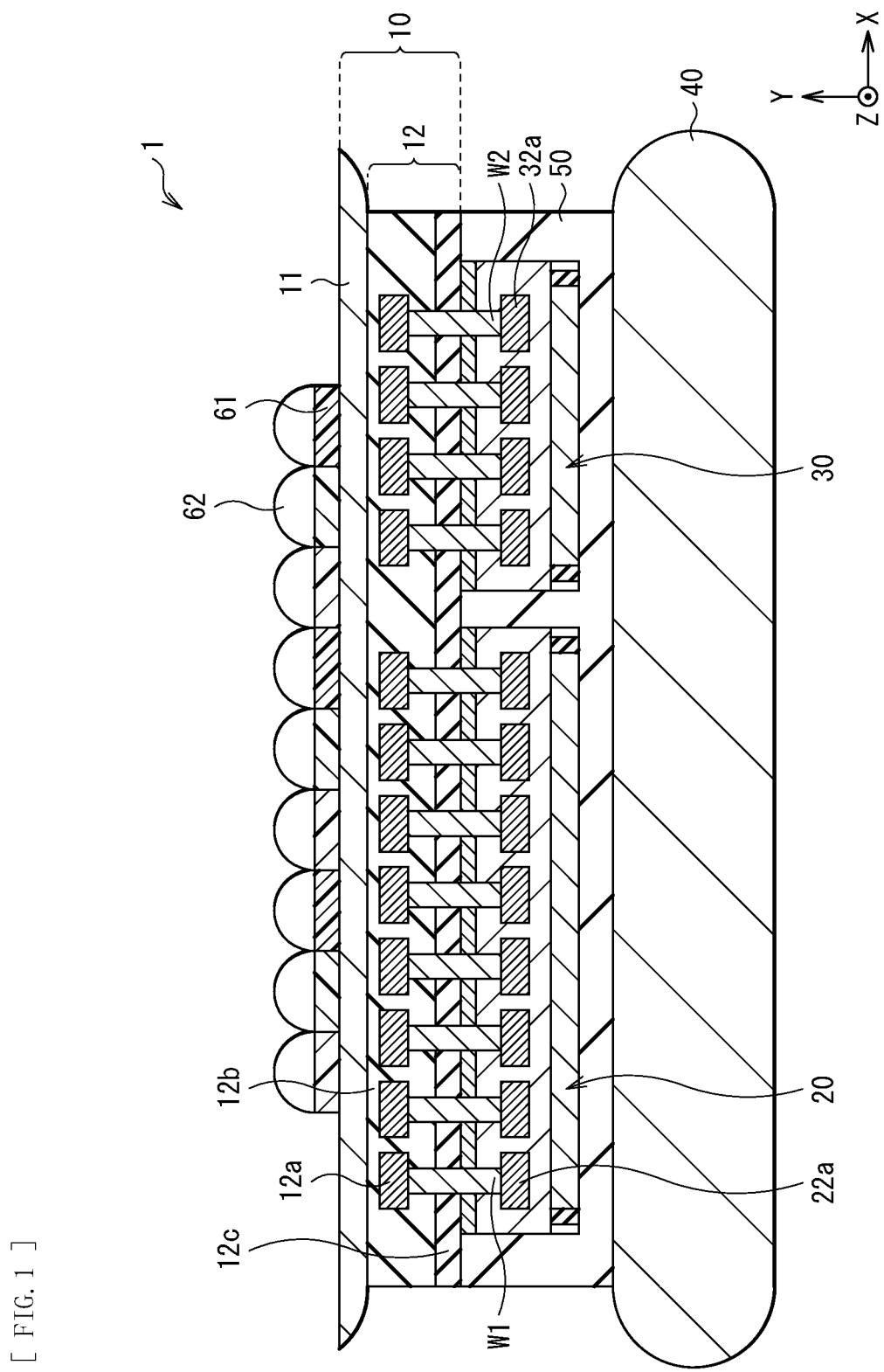
[ FIG. 1 ]

[ FIG. 2 ]
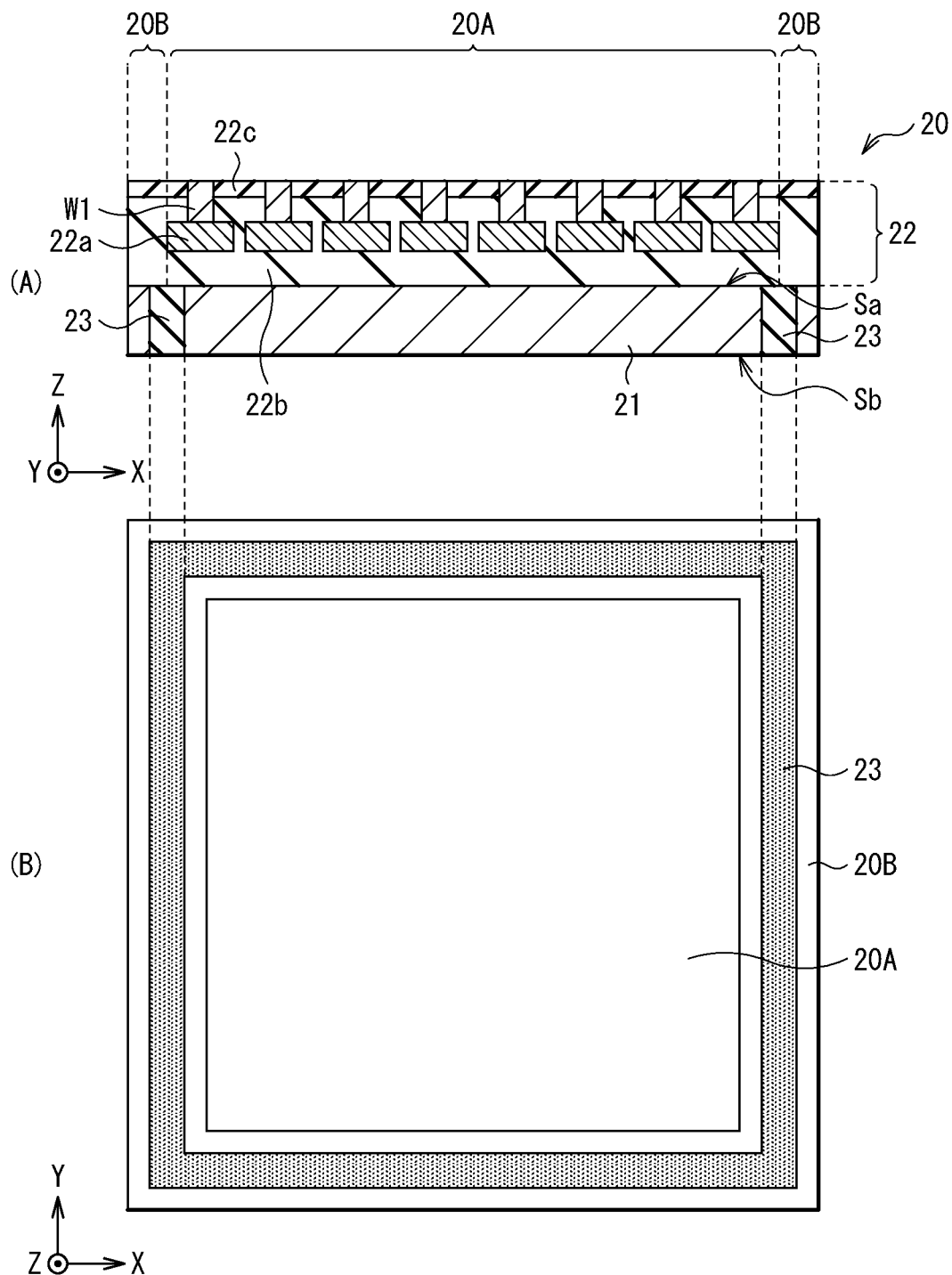

[ FIG. 3 ]
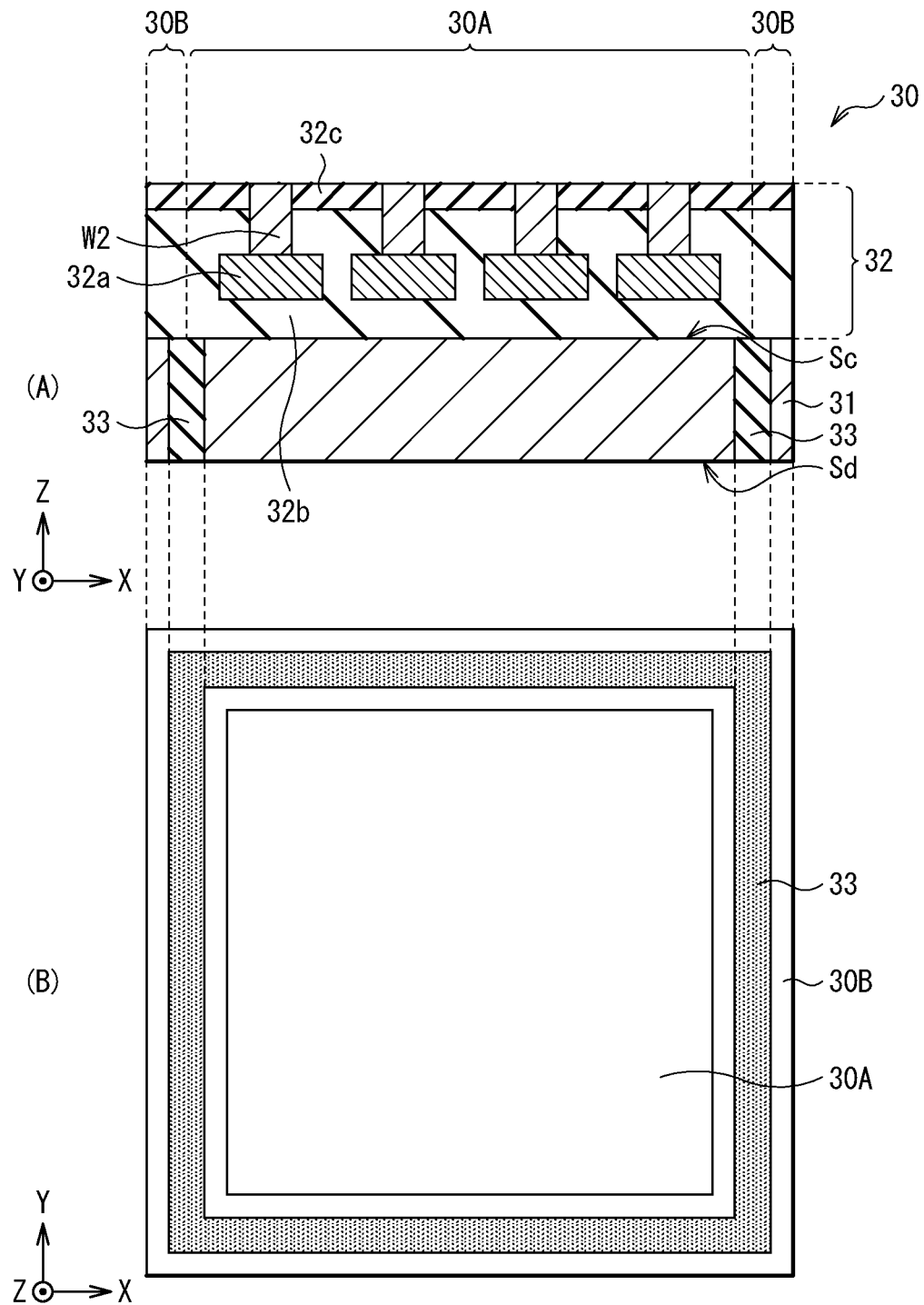

[ FIG. 4 ]
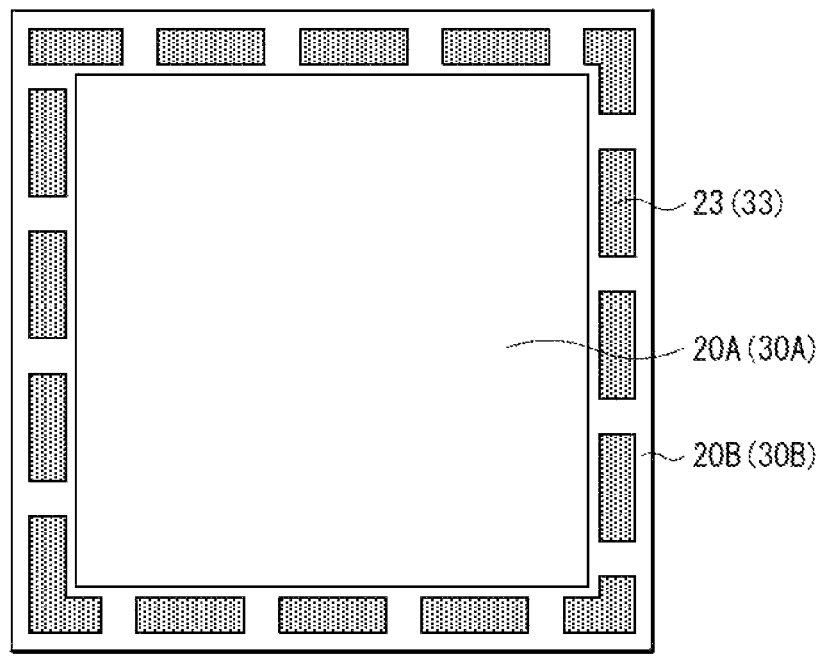
[ FIG. 5 ]
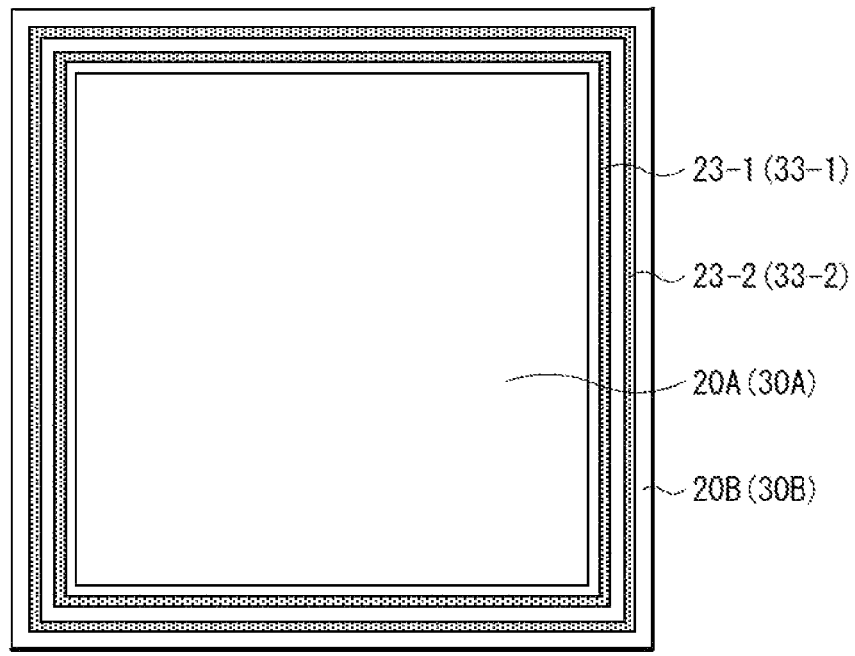

[ FIG. 6 ]
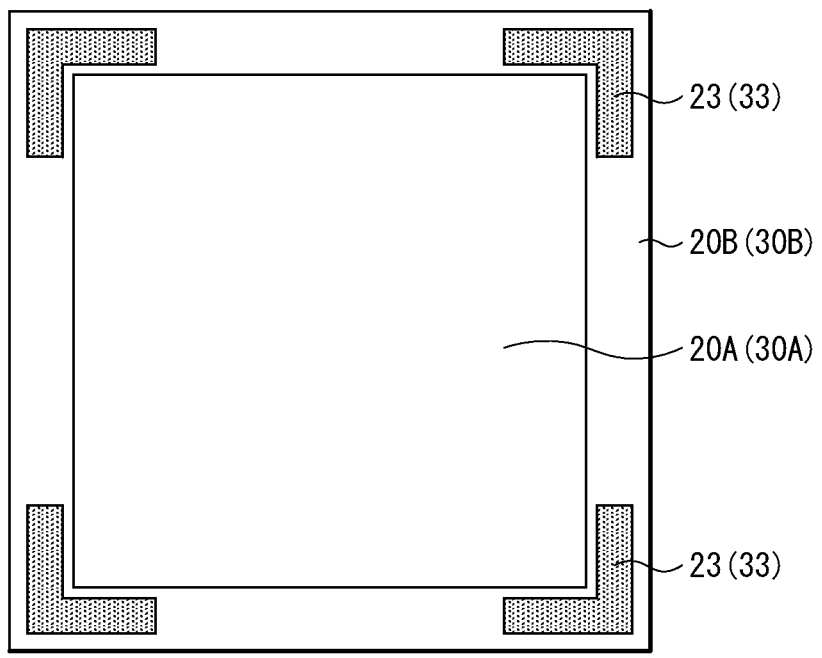

[ FIG. 7 ]
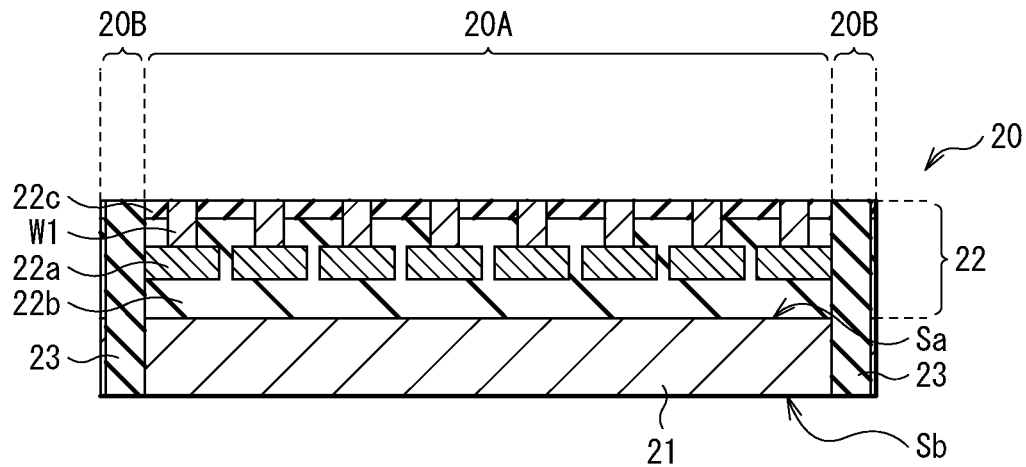
[ FIG. 8 ]
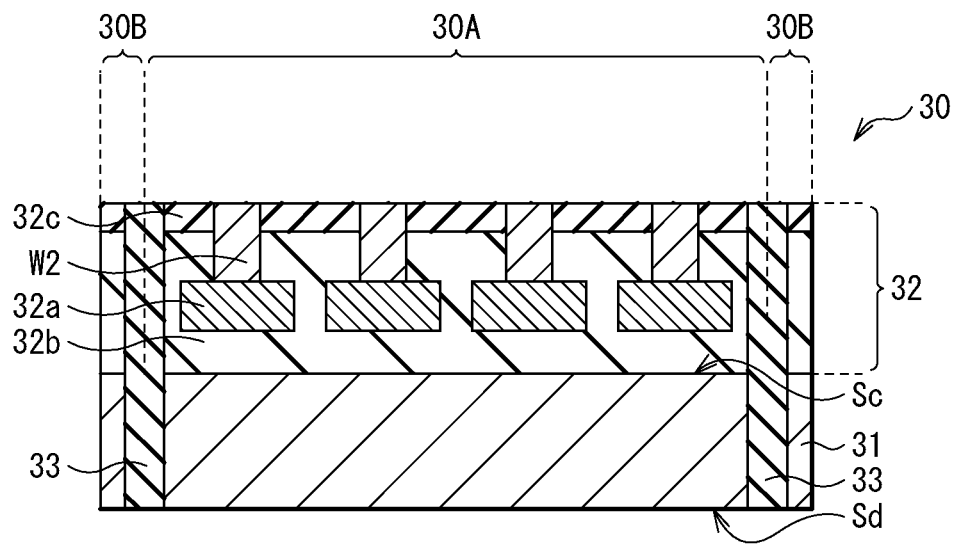

[ FIG. 9A ]
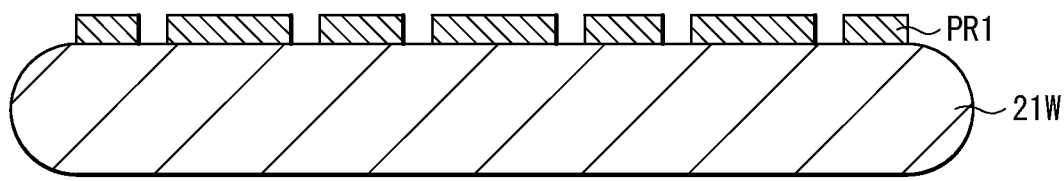
[ FIG. 9B ]
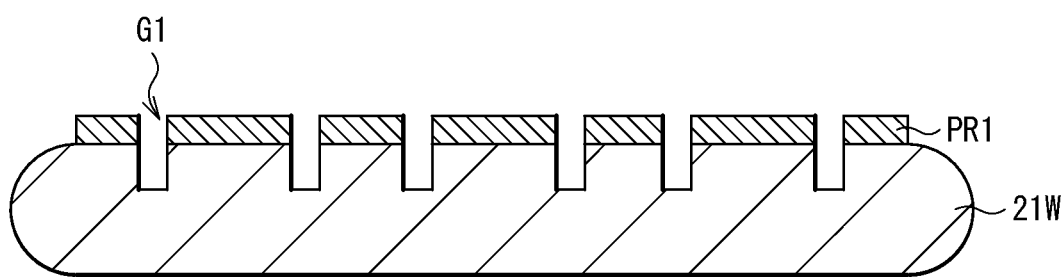
[ FIG. 9C ]
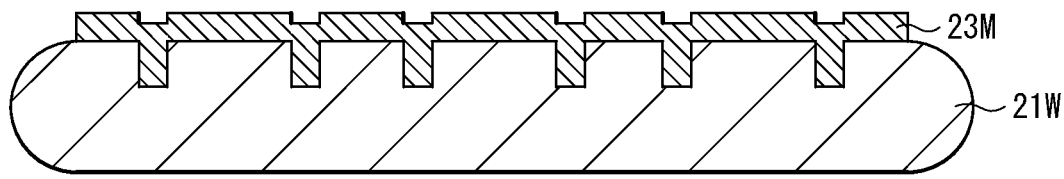

[ FIG. 9D ]
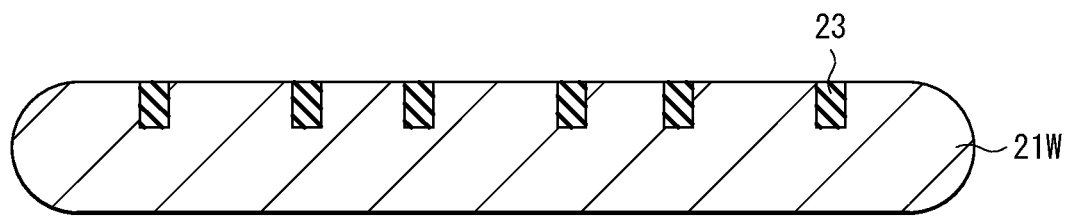
[ FIG. 9E ]
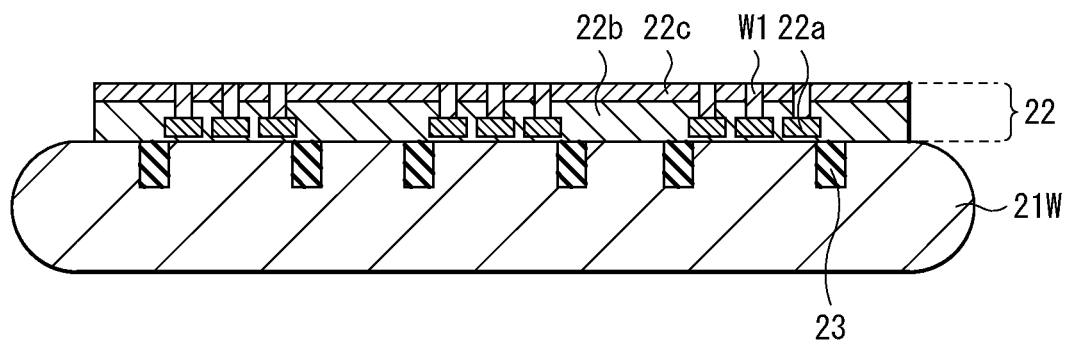
[ FIG. 9F ]
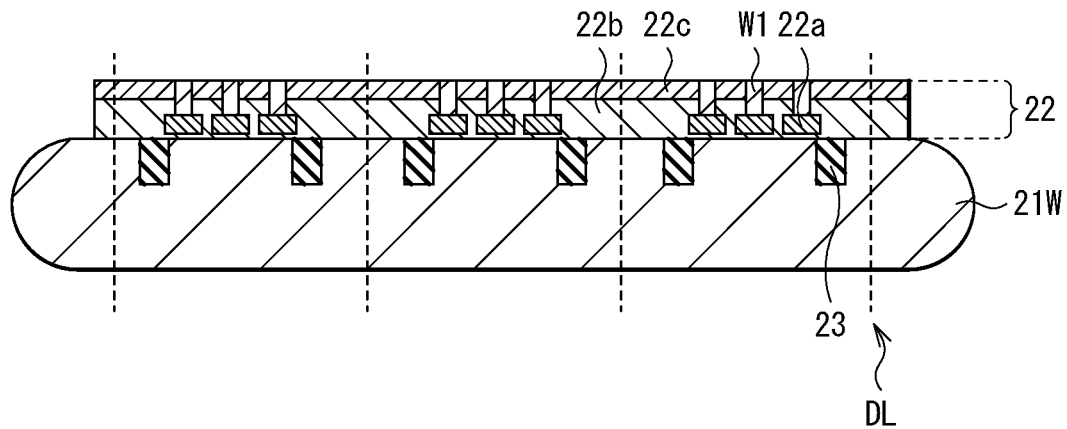

[ FIG. 9G ]
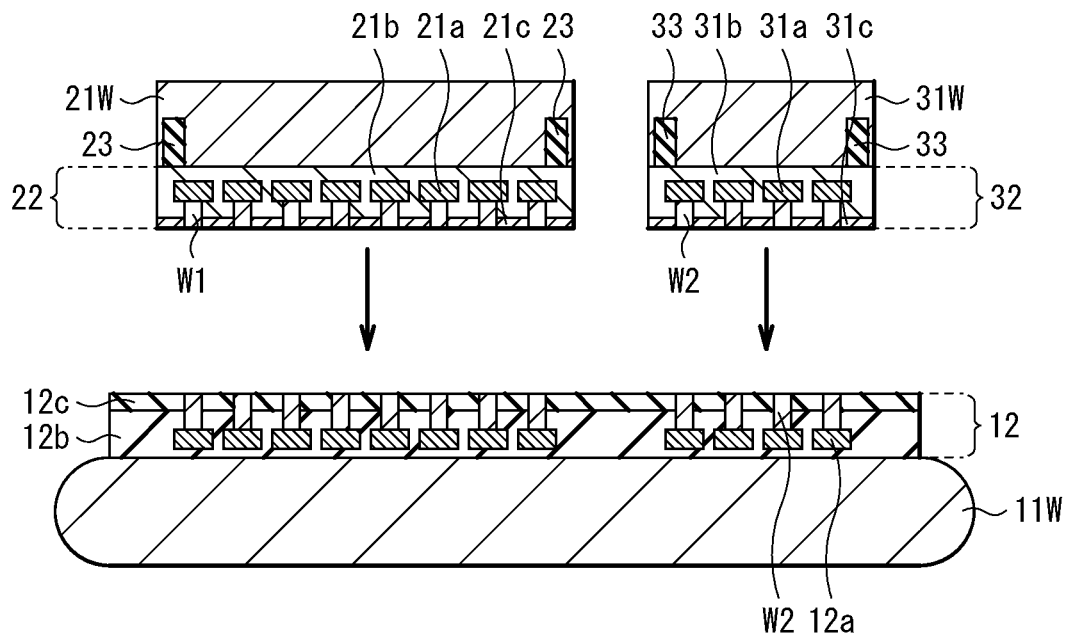
[ FIG. 9H ]
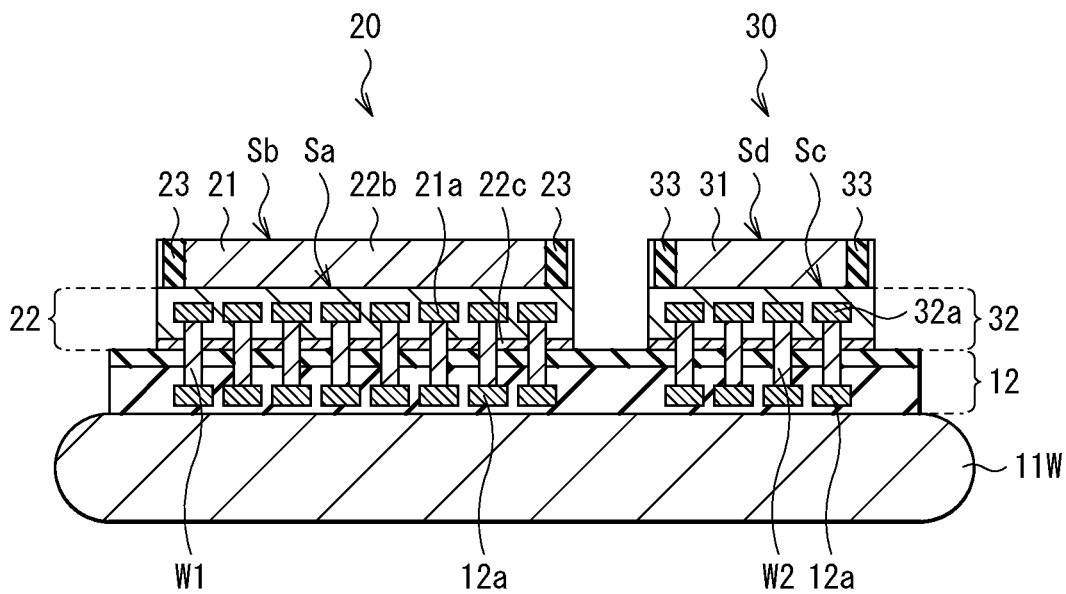

[ FIG. 10A ]
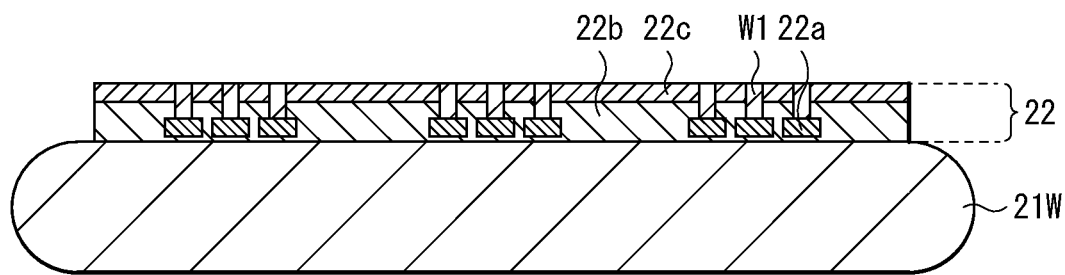
[ FIG. 10B ]
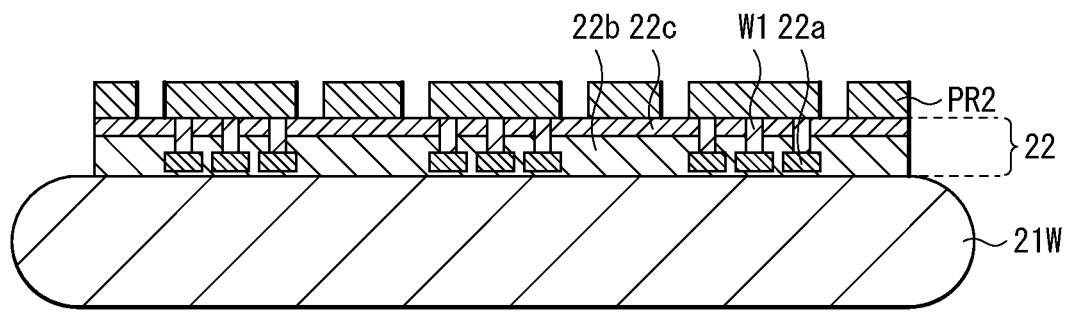
[ FIG. 10C ]
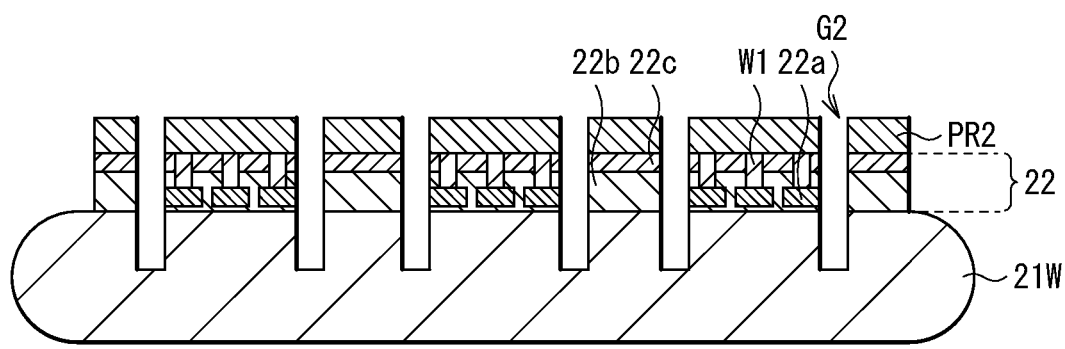

[ FIG. 10D ]
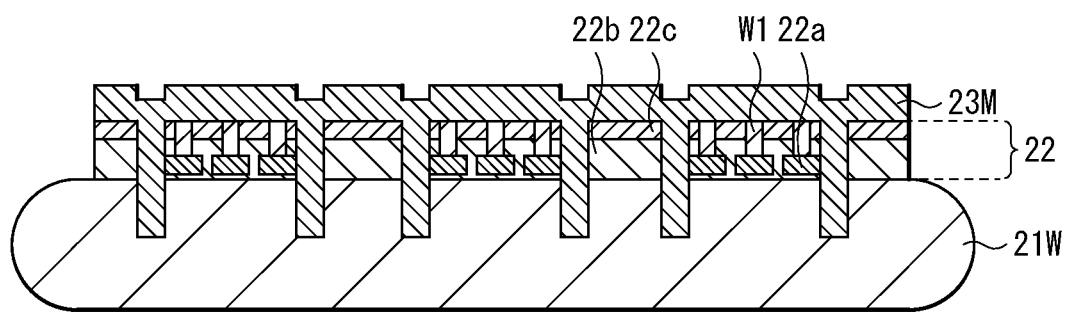
[ FIG. 10E ]
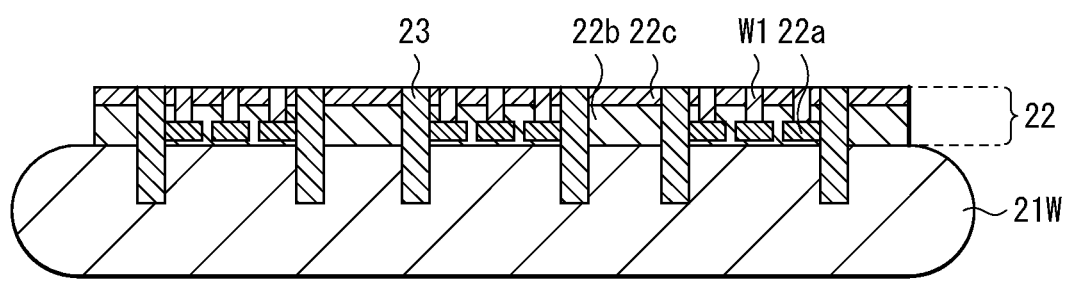

[ FIG. 11A ]
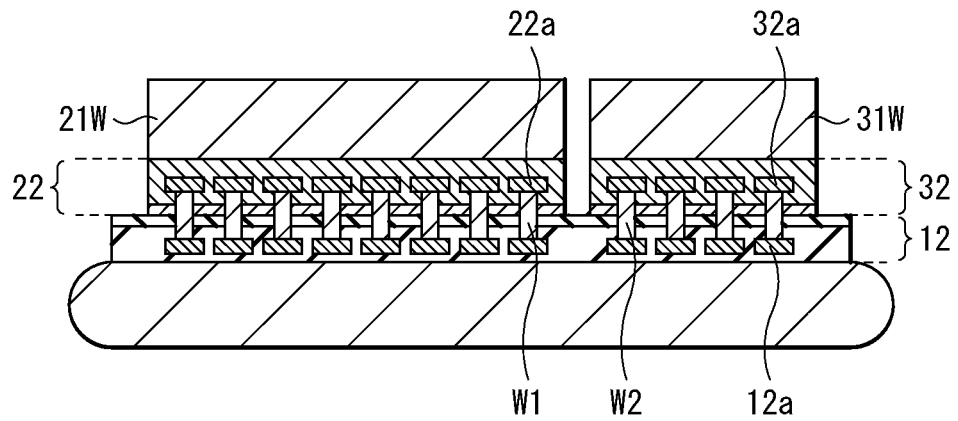
[ FIG. 11B ]
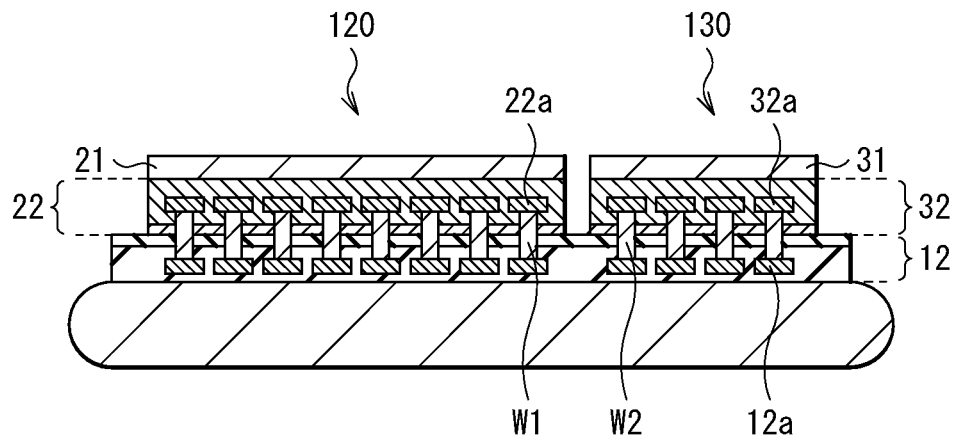
[ FIG. 12 ]
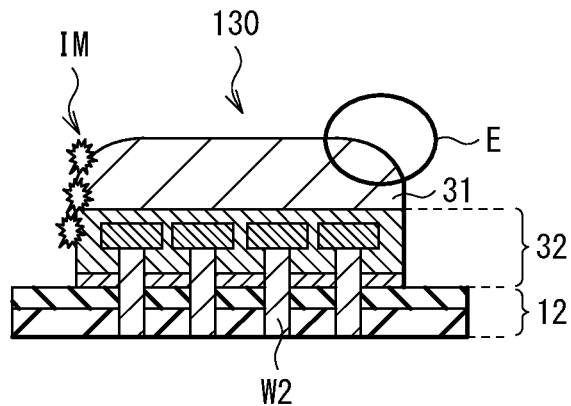

[ FIG. 13 ]
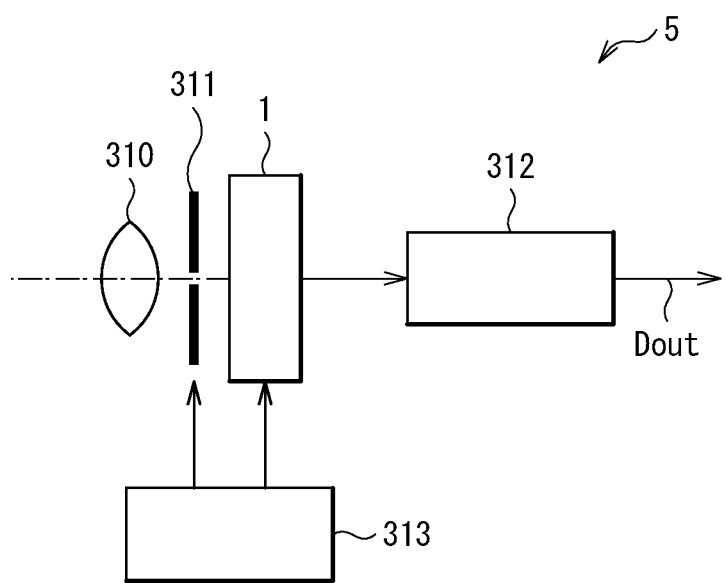

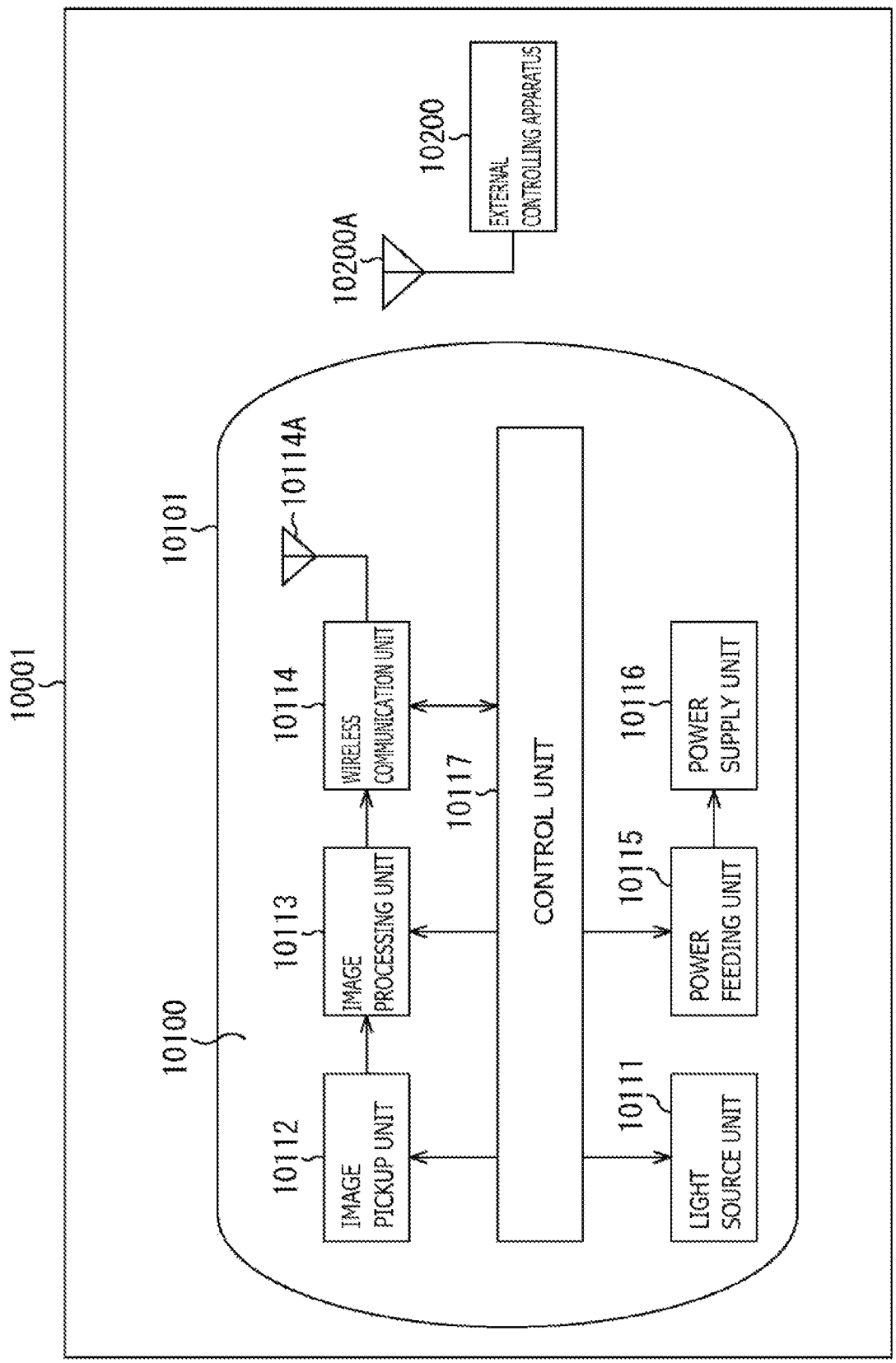
[ FIG. 14 ]

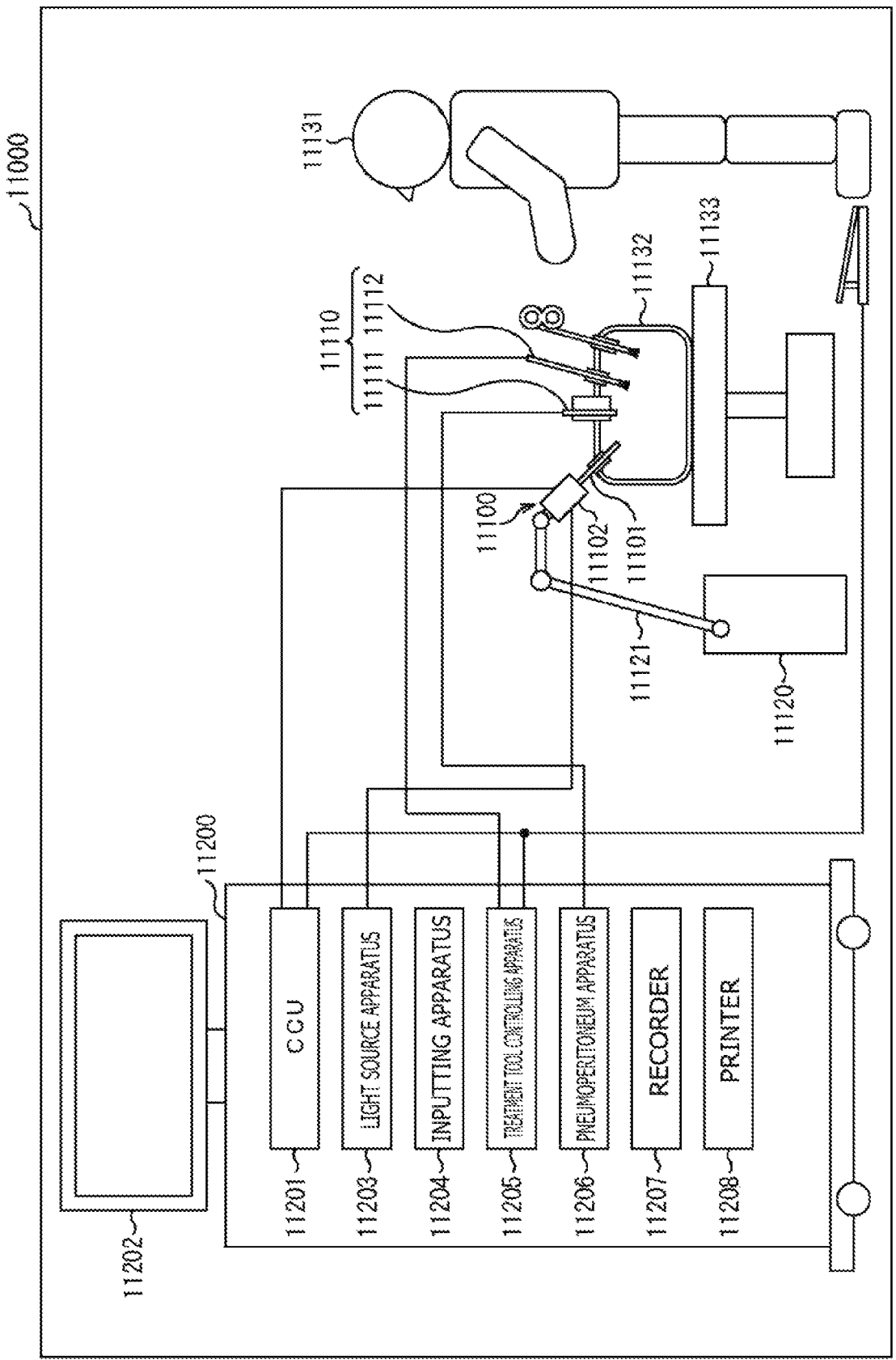
[FIG. 15]

[ FIG. 16 ]
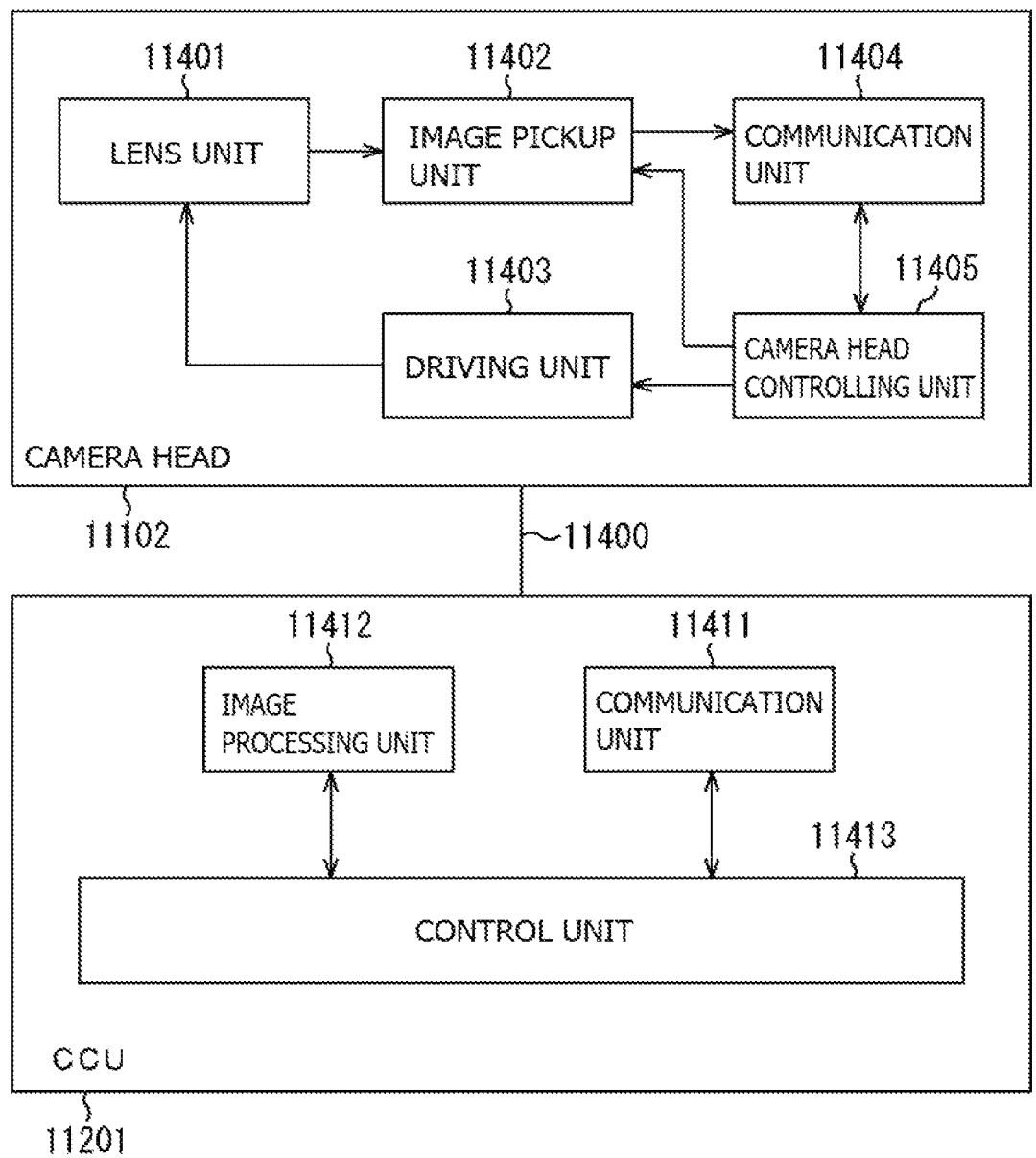

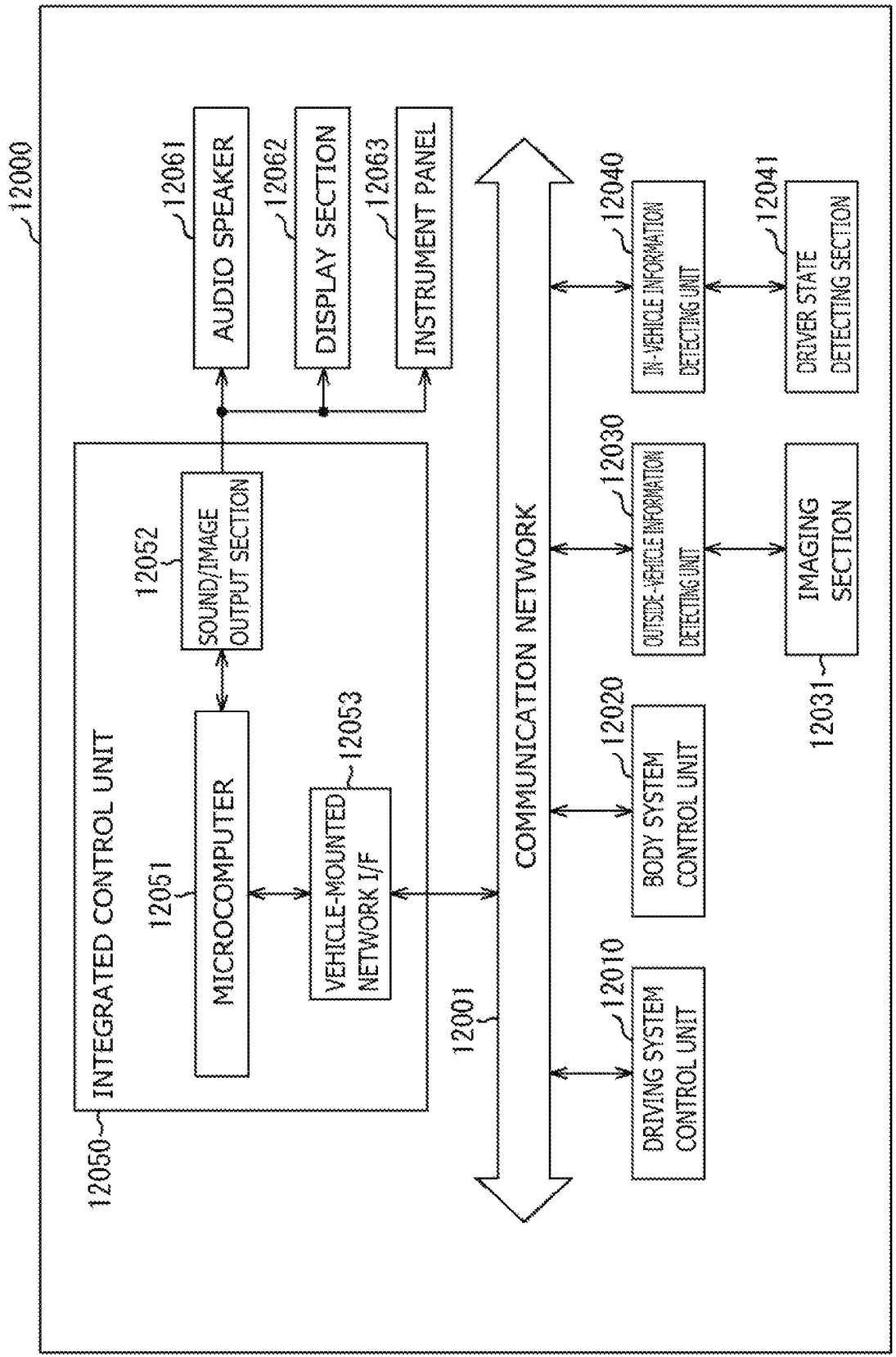
[ FIG. 17 ]

[ FIG. 18 ]
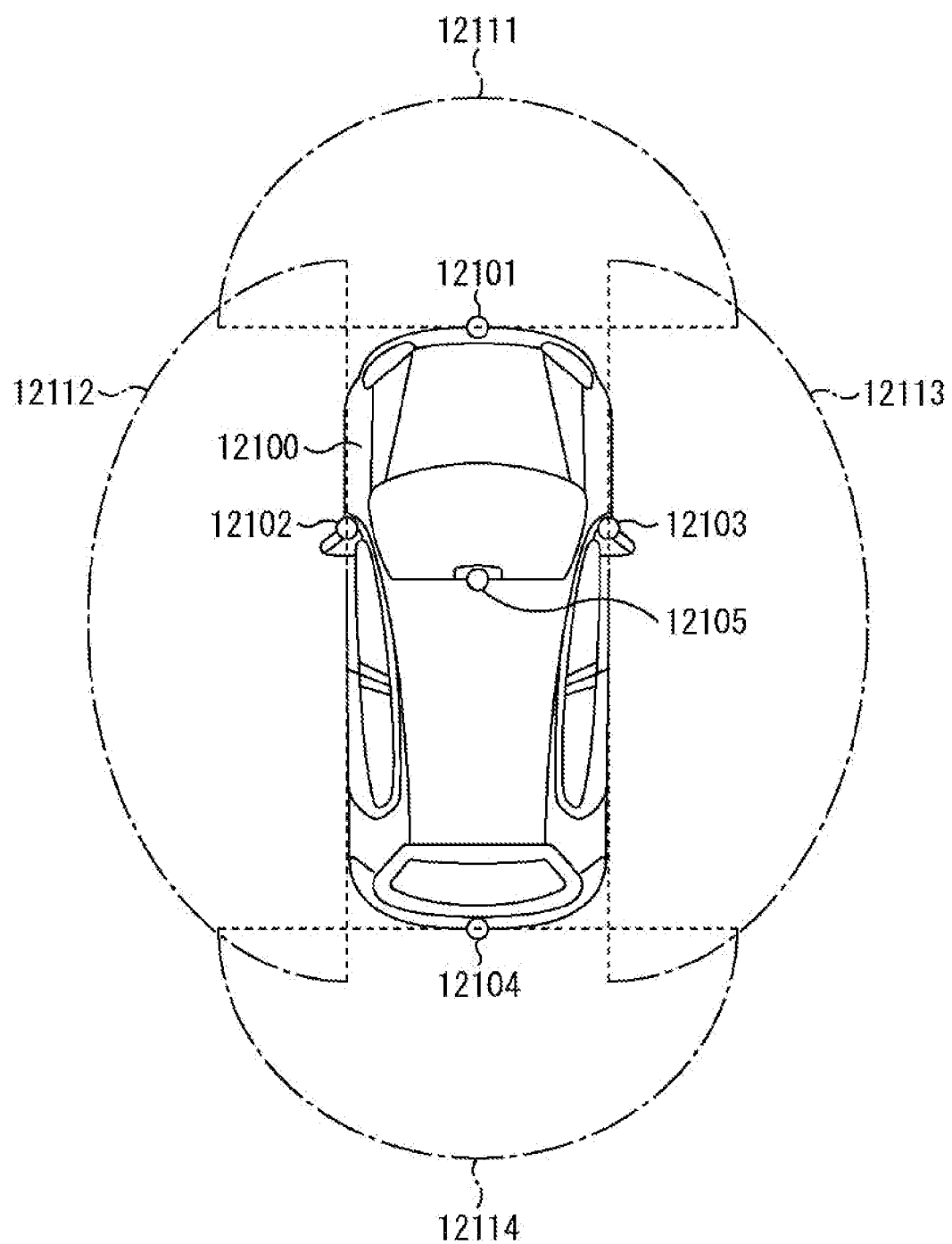

IMAGE DEVICE

TECHNICAL FIELD

The present disclosure relates to an imaging device including an imaging element and a semiconductor element.

BACKGROUND ART

For example, a solid-state imaging device has been proposed in which an imaging element and a semiconductor element are stacked (see, for example, Patent Literature 1). In this solid-state imaging device, for example, stacked are the imaging element with a PD (Photo Diode) or the like provided for each pixel and the semiconductor element provided with a circuit that processes a signal obtained at each pixel. The semiconductor element includes a semiconductor substrate and a wiring layer, for example.

CITATION LIST

Patent Literature

PTL 1: Japanese Unexamined Patent Application Publication No. 2014-099582

SUMMARY OF THE INVENTION

Regarding such an imaging device of a stacked type, there is a concern that reliability or the like can be reduced due to a defect during manufacture.

Therefore, it is desirable to provide an imaging device that makes it possible to suppress the occurrence of a detect during manufacture.

An imaging device according to an embodiment of the present disclosure includes an imaging element, and a semiconductor element provided to be opposed to the imaging element and electrically coupled to the imaging element. The semiconductor element includes: a wiring region provided in a middle portion and a peripheral region outside the wiring region; a wiring layer having a wiring line in the wiring region; a semiconductor substrate opposed to the imaging element with the wiring layer interposed therebetween and having a first surface and a second surface in order from a side of the wiring layer; and a polishing adjustment section including a material that is lower in polishing rate than a constituent material of the semiconductor substrate, the polishing adjustment section being disposed in at least a portion of the peripheral region and provided in a thickness direction of the semiconductor substrate from the second surface.

In the imaging device according to the embodiment of the present disclosure, the polishing adjustment section is provided in the semiconductor element, and this suppresses excessive polishing of the peripheral region when the semiconductor substrate is polished in a process of manufacturing the imaging device.

BRIEF DESCRIPTION OF DRAWINGS

FIG. 1 is a schematic cross-sectional diagram illustrating a configuration of an imaging device according to an embodiment of the present disclosure.

FIG. 2 (A) of FIG. 2 is a schematic cross-sectional diagram illustrating a configuration of a memory chip illustrated in FIG. 1, and (B) of FIG. 2 is a schematic diagram illustrating a planar configuration of a main part of (A).

FIG. 3 (A) of FIG. 3 is a schematic cross-sectional diagram illustrating a configuration of a logic chip illustrated in FIG. 1, and (B) of FIG. 3 is a schematic diagram illustrating a planar configuration of a main part of (A).

FIG. 4 is a schematic diagram illustrating another example (1) of a planar configuration of a polishing adjustment section illustrated in FIGS. 2 and 3.

FIG. 5 is a schematic diagram illustrating another example (2) of the planar configuration of the polishing adjustment section illustrated in FIGS. 2 and 3.

FIG. 6 is a schematic diagram illustrating another example (3) of the planar configuration of the polishing adjustment section illustrated in FIGS. 2 and 3.

FIG. 7 is a schematic diagram illustrating another example of the cross-sectional configuration of the memory chip illustrated in (A) of FIG. 2.

FIG. 8 is a schematic diagram illustrating another example of the cross-sectional configuration of the logic chip illustrated in (A) of FIG. 3.

FIG. 9A is a schematic cross-sectional diagram illustrating a step of a method of manufacturing the imaging device illustrated in FIG. 1.

FIG. 9B is a schematic cross-sectional diagram illustrating a step that follows FIG. 9A.

FIG. 9C is a schematic cross-sectional diagram illustrating a step that follows FIG. 9B.

FIG. 9D is a schematic cross-sectional diagram illustrating a step that follows FIG. 9C.

FIG. 9E is a schematic cross-sectional diagram illustrating a step that follows FIG. 9D.

FIG. 9F is a schematic cross-sectional diagram illustrating a step that follows FIG. 9E.

FIG. 9G is a schematic cross-sectional diagram illustrating a step that follows FIG. 9F.

FIG. 9H is a schematic cross-sectional diagram illustrating a step that follows FIG. 9G.

FIG. 10A is a schematic cross-sectional diagram illustrating another example of the method of manufacturing the imaging device illustrated in FIG. 1.

FIG. 10B is a schematic cross-sectional diagram illustrating a step that follows FIG. 10A.

FIG. 10C is a schematic cross-sectional diagram illustrating a step that follows FIG. 10B.

FIG. 10D is a schematic cross-sectional diagram illustrating a step that follows FIG. 10C.

FIG. 10E is a schematic cross-sectional diagram illustrating a step that follows FIG. 10D.

FIG. 11A is a schematic cross-sectional diagram illustrating a step of a method of manufacturing an imaging device according to a comparative example.

FIG. 11B is a schematic cross-sectional diagram illustrating a step that follows FIG. 11A.

FIG. 12 is a schematic cross-sectional diagram illustrating a configuration of a logic chip illustrated in FIG. 11B on an enlarged scale.

FIG. 13 is a functional block diagram illustrating an example of an electronic apparatus including the imaging device illustrated in FIG. 1, etc.

FIG. 14 is a block diagram depicting an example of a schematic configuration of an in-vivo information acquisition system.

FIG. 15 is a view depicting an example of a schematic configuration of an endoscopic surgery system.

FIG. 16 is a block diagram depicting an example of a functional configuration of a camera head and a camera control unit (CCU).

FIG. 17 is a block diagram depicting an example of schematic configuration of a vehicle control system.

FIG. 18 is a diagram of assistance in explaining an example of installation positions of an outside-vehicle information detecting section and an imaging section.

MODES FOR CARRYING OUT THE INVENTION

In the following, an embodiment of the present disclosure will be described in detail with reference to the drawings. It is to be noted that the description is given in the following order.

1. Embodiment (an imaging device including a polishing adjustment section in a semiconductor element)
2. Application Example (an electronic apparatus)
3. Example of Practical Application

Embodiment (Configuration of Imaging Device 1)

FIG. 1 schematically illustrates an example of a cross-sectional configuration of a solid-state imaging device (an imaging device 1) according to an example of the present disclosure. This imaging device 1 is, for example, a back-illumination type CMOS (Complementary Metal Oxide Semiconductor) image sensor. The imaging device 1 includes mainly an imaging element 10, a memory chip 20, and a logic chip 30. The memory chip 20 and the logic chip 30 are provided on a support substrate 40. The imaging element 10 is opposed to the support substrate 40 with the memory chip 20 and the logic chip 30 interposed therebetween. Between the support substrate 40 and the imaging element 10, there is provided a buried layer 50 together with the memory chip 20 and the logic chip 30. A color filter 61 and an on-chip lens 62 are provided on a light entrance side (a side opposite to a surface facing the memory chip 20 and the logic chip 30) of the imaging element 10. Here, the memory chip 20 and the logic chip 30 correspond to a specific example of a "semiconductor element" of the present disclosure.

The imaging element 10 is larger in chip size than each of the memory chip 20 and the logic chip 30, for example. Specifically, a planar shape of the imaging element 10 is larger in size than a planar shape of each of the memory chip 20 and the logic chip 30. The imaging element 10 includes, for example, a semiconductor substrate 11 and a wiring layer 12. The semiconductor substrate 11 is opposed to the memory chip 20 and the logic chip 30 with the wiring layer 12 interposed therebetween, for example. On the semiconductor substrate 11, a PD (a photoelectric converter) is provided for each pixel. The semiconductor substrate 11 is configured by, for example, a silicon (Si) substrate. The wiring layer 12 is provided between the semiconductor substrate 11 and the memory chip 20, and between the semiconductor substrate 11 and the logic chip 30. The wiring layer 12 includes, for example, a terminal 12a, a first insulating film 12b, and a second insulating film 12c. The first insulating film 12b and the second insulating film 12c are stacked in this order from the semiconductor substrate 11 side. For example, the first insulating film 12b has a thickness larger than a thickness of the second insulating film 12c. The first insulating film 12b and the second insulating film 12c include, for example, silicon oxide (SiO) or the like. A plurality of the terminals 12a are provided in the wiring layer 12, and the plurality of terminals 12a are separated from each other by the first insulating film 12b. Ones of the plurality of terminals 12a that are provided at positions opposed to the memory chip 20 are each electrically coupled to the memory chip 20 (more specifically, a terminal 22a to be described later) by a wiring line W1. Ones of the plurality of terminals 12a that are provided at positions opposed to the logic chip 30 are each electrically coupled to the logic chip 30 (more specifically, a terminal 32a to be described later) by a wiring line W2. The terminals 12a include, for example, copper (Cu), aluminum (Al), or the like.

FIG. 2 illustrates a more specific configuration of the memory chip 20. (A) of FIG. 2 illustrates a cross-sectional configuration of the memory chip 20, and (B) of FIG. 2 illustrates a planar configuration of a main part of the memory chip 20.

The memory chip 20 provided to be opposed to the imaging element 10 includes a wiring region 20A in a middle portion, and a peripheral region 20B provided outside the wiring region 20A to surround the wiring region 20A. For example, the wiring region 20A is a region that effectively functions as the memory chip 20, and in this wiring region 20A, the memory chip 20 has a memory circuit electrically coupled to the PD of the imaging element 10. The wiring region 20A has a planar shape (shape in an XY plane in (B) of FIG. 2) that is quadrangular, for example.

The memory chip 20 includes, for example, a semiconductor substrate 21 and a wiring layer 22. Here, the semiconductor substrate 21 or a semiconductor substrate 31 to be described later corresponds to one specific example of a "semiconductor substrate" of the present disclosure, and the wiring layer 22 or a wiring layer 32 to be described later corresponds to one specific example of a "wiring layer" of the present disclosure. The semiconductor substrate 21 and the wiring layer 22 are provided across the wiring region 20A and the peripheral region 20B. The semiconductor substrate 21 is, for example, opposed to the imaging element 10 with the wiring layer 22 interposed therebetween, and has a front surface Sa on the wiring layer 22 side, and a back surface Sb provided opposite to the front surface Sa. A plurality of MOS (Metal Oxide Semiconductor) transistors (not illustrated) is provided in the wiring region 20A of the semiconductor substrate 21. The memory circuit is configured using the plurality of MOS transistors, for example. The semiconductor substrate 21 is configured by a silicon (Si) substrate, for example. The wiring layer 22 is provided between the semiconductor substrate 21 and the imaging element 10, that is, on the front surface Sa side of the semiconductor substrate 21. The wiring layer 22 includes, for example, the terminal 22a, a first insulating film 22b, and a second insulating film 22c. The first insulating film 22b and the second insulating film 22c are stacked in this order from the semiconductor substrate 21 side. For example, the first insulating film 22b has a thickness larger than a thickness of the second insulating film 22c. The first insulating film 22b and the second insulating film 22c include, for example, silicon oxide (SiO) or the like. A plurality of the terminals 22a are provided in the wiring region 20A, and the plurality of terminals 22a are separated from each other by the first insulating film 22b. The plurality of terminals 22a are electrically coupled to the terminals 12a of the imaging element 10, each by the wiring line W1. The terminals 22a include, for example, copper (Cu), aluminum (Al), or the like. The wiring line W1 is configured by, for example, a CuCu junction between a pad on the memory chip 20 side and a pad on the imaging element 10 side. Here, the terminal 22a or the terminal 22a to be described later corresponds to one specific example of a "wiring line" of the present disclosure.

In the present embodiment, the memory chip 20 further includes a polishing adjustment section 23. The polishing adjustment section 23 is disposed in the peripheral region 20B, and is provided across a thickness direction (a Z direction in (A) of FIG. 2) of the semiconductor substrate 21 from the back surface Sb. The polishing adjustment section 23 includes a material that is lower in polishing rate than the constituent material of the semiconductor substrate 21. As will be described in detail later, providing such a polishing adjustment section 23 in the memory chip 20 suppresses excessive polishing of the peripheral region 20B of the semiconductor substrate 21 in a process of polishing the semiconductor substrate 21 in forming the memory chip 20.

In a case where the semiconductor substrate 21 is configured by a silicon (Si) substrate, the polishing adjustment section 23 includes, for example, silicon nitride (SiN), silicon oxide (SiO), or the like. The polishing adjustment section 23 is provided, for example, across the thickness direction of the semiconductor substrate 21 from the back surface Sb to the front surface Sa. The polishing adjustment section 23 is exposed in the back surface Sb of the semiconductor substrate 21, for example. The polishing adjustment section 23 is provided, for example, to surround the wiring region 20A, and is shaped like a frame in planar shape. The polishing adjustment section 23 is preferably provided to surround the wiring region 20A. This makes it possible to suppress excessive polishing of the semiconductor substrate 21 in all directions.

FIG. 3 illustrates a more specific configuration of the logic chip 30. (A) of FIG. 3 illustrates a cross-sectional configuration of the logic chip 30, and (B) of FIG. 3 illustrates a planar configuration of a main part of the logic chip 30.

The logic chip 30 provided to be opposed to the imaging element 10 includes a wiring region 30A in a middle portion, and a peripheral region 30B provided outside the wiring region 30A to surround the wiring region 30A. For example, the wiring region 30A is a region that effectively functions as the logic chip 30, and in this wiring region 30A, the logic chip 30 has a logic circuit electrically coupled to the PD of the imaging element 10. The wiring region 30A has a planar shape (shape in the XY plane in (B) of FIG. 3) that is quadrangular, for example. The planar shape of the logic chip 30 is smaller than the planar shape of the memory chip 20, for example.

The logic chip 30 includes, for example, the semiconductor substrate 31 and the wiring layer 32. The semiconductor substrate 31 and the wiring layer 32 are provided across the wiring region 30A and the peripheral region 30B. The semiconductor substrate 31 is, for example, opposed to the imaging element 10 with the wiring layer 32 interposed therebetween, and has a front surface Sc on the wiring layer 32 side, and a back surface Sd provided opposite to the front surface Sc. A plurality of MOS transistors (not illustrated) is provided in the wiring region 30A of the semiconductor substrate 31. The logic circuit is configured using the plurality of MOS transistors, for example. The semiconductor substrate 31 is configured by a silicon (Si) substrate, for example. The wiring layer 32 is provided between the semiconductor substrate 31 and the imaging element 10, that is, on the front surface Sc side of the semiconductor substrate 31. The wiring layer 32 includes, for example, the terminal 32a, a first insulating film 32b, and a second insulating film 32c. The first insulating film 32b and the second insulating film 32c are stacked in this order from the semiconductor substrate 31 side. For example, the first insulating film 32b has a thickness larger than a thickness of the second insulating film 32c. The first insulating film 32b and the second insulating film 32c include, for example, silicon oxide (SiO). A plurality of the terminals 32a are provided in the wiring region 30A, and the plurality of terminals 32a are separated from each other by the first insulating film 32b. The plurality of terminals 32a are electrically coupled to the terminals 12a of the imaging element 10, each by the wiring line W2. The terminals 32a include, for example, copper (Cu), aluminum (Al), or the like. The wiring line W2 is configured by, for example, a CuCu junction between a pad on the logic chip 30 side and a pad on the imaging element 10 side.

The logic chip 30 further includes a polishing adjustment section 33. The polishing adjustment section 33 is disposed in the peripheral region 30B, and is provided across the thickness direction (the Z direction in (A) of FIG. 3) of the semiconductor substrate 31 from the back surface Sd. The polishing adjustment section 33 includes a material that is lower in polishing rate than the constituent material of the semiconductor substrate 31. As with the polishing adjustment section 23 of the memory chip 20 described above, providing the polishing adjustment section 33 suppresses excessive polishing of the peripheral region 30B of the semiconductor substrate 31 in a process of polishing the semiconductor substrate 31 in forming the logic chip 30.

In a case where the semiconductor substrate 31 is configured by a silicon (Si) substrate, the polishing adjustment section 33 includes, for example, silicon nitride (SiN), silicon oxide (SiO), or the like. The polishing adjustment section 33 is provided, for example, across the thickness direction of the semiconductor substrate 31 from the back surface Sd to the front surface Sc. The polishing adjustment section 33 is exposed in the back surface Sd of the semiconductor substrate 31, for example. The polishing adjustment section 33 is provided, for example, to surround the wiring region 30A, and is shaped like a frame in planar shape. The polishing adjustment section 33 is preferably provided to surround the wiring region 30A. This makes it possible to suppress excessive polishing of the semiconductor substrate 31 in all directions.

FIGS. 4 to 6 illustrate other examples of the planar shapes of the polishing adjustment sections 23 and 33. The polishing adjustment sections 23 and 33 may not be provided continuously. For example, as illustrated in FIG. 4, a plurality of the polishing adjustment sections 23 or 33 may be provided separately from each other around the wiring region 20A or 30A.

As illustrated in FIG. 5, the polishing adjustment sections 23 and 33 may include first polishing adjustment sections 23-1 and 33-1 and second polishing adjustment sections 23-2 and 33-2. The first polishing adjustment sections 23-1 and 33-1 are, for example, provided at a position near the wiring regions 20A and 30A and surround the wiring regions 20A and 30A. The second polishing adjustment sections 23-2 and 33-2 are, for example, provided at a position farther from the wiring regions 20A and 30A than the first polishing adjustment sections 23-1 and 33-1, and surround the wiring regions 20A and 30A.

As illustrated in FIG. 6, the polishing adjustment sections 23 and 33 may be provided in part of the peripheral regions 20B and 30B. In this case, the polishing adjustment sections 23 and 33 are preferably provided at corners of the semiconductor substrates 21 and 31 that are quadrangular in planar shape. At the corners of the semiconductor substrates 21 and 31, excessive polishing tends to occur. Providing the polishing adjustment sections 23 and 33 at the corners makes it possible to effectively suppress the excessive polishing.

FIG. 7 illustrates another example of the cross-sectional configuration of the memory chip 20, and FIG. 8 illustrates another example of the cross-sectional configuration of the logic chip 30. As illustrated, the polishing adjustment sections 23 and 33 may be provided across the semiconductor substrates 21 and 31 and the wiring layers 22 and 32. The polishing adjustment sections 23 and 33 are, for example, exposed in the back surfaces Sb and Sd of the semiconductor substrates 21 and 31, and are also exposed in surfaces of the wiring layers 22 and 32 facing the imaging element 1.

The support substrate 40 supports such a memory chip 20 and logic chip 30 (FIG. 1). The support substrate 40 is, for example, to ensure strengths of the memory chip 20 and the logic chip 30 in the manufacturing stage, and is configured by a silicon (Si) substrate, for example.

The memory chip 20 and the logic chip 30 provided on the support substrate 40 are covered with the buried layer 50 (FIG. 1). The buried layer 50 covers the memory chip 20 and the logic chip 30, and is provided around each of the memory chip 20 and the logic chip 30. The buried layer 50 has a flat surface, and the imaging element 10 is provided in contact with the flat surface. The flat surface of the buried layer 50 is formed by, for example, a planarization process such as CMP (Chemical Mechanical Polishing). The buried layer 50 includes an insulating film of, for example, silicon oxide (SiO) or the like. The buried layer 50 may be provided between the support substrate 40 and the memory chip 20 or between the support substrate 40 and the logic chip 30.

For example, the imaging element 10, the color filter 61, and the on-chip lens 62 are provided in this order on the buried layer 50. The color filter 61 provided on the light entrance side of the imaging element 10 is, for example, any one of a red (R) filter, a green (G) filter, a blue (B) filter, and a white (W) filter, and is provided for each pixel. These color filters 61 are provided in a regular color arrangement (for example, a Bayer arrangement). Providing such color filters 61 allows the imaging device 1 to obtain light reception data of a color corresponding to the color arrangement.

The on-chip lens 62 on the color filter 61 is provided at a position opposed to the PD of the imaging element 10 for each pixel. Light having entered the on-chip lens 62 is condensed on the PD for each pixel. A lens system of the on-chip lens 62 is set at a value corresponding to a size of the pixel. Examples of a lens material for the on-chip lens 62 include an organic material, a silicon oxide film (SiO), and the like.

(Method of Manufacturing Imaging Device 1)

Such an imaging device 1 may be manufactured in the following manner (FIGS. 9A to 9H), for example. Here, a process of manufacturing the memory chip 20 will be mainly described.

First, as illustrated in FIG. 9A, a photoresist PR1 patterned into a predetermined shape is formed on a semiconductor substrate 21W in wafer form. In a later step, the semiconductor substrate 21W is to be divided into pieces (FIG. 9F to be described later), and is further to be polished to form the semiconductor substrate 21 (FIG. 9H to be described later) of the memory chip 20. The semiconductor substrate 21W is configured by a silicon (Si) substrate, for example.

Subsequently, as illustrated in FIG. 9B, a plurality of grooves G1 is formed in the semiconductor substrate 21W using the photoresist PR1. The grooves G1 are for forming the polishing adjustment section 23 of the memory chip 20. The plurality of grooves G1 shaped like a frame (see (B) of FIG. 2), for example, is formed in the semiconductor substrate 21W.

After the grooves G1 are formed, as illustrated in FIG. 9C, a polishing adjustment material 23M is formed into a film on the semiconductor substrate 21W. The polishing adjustment material 23M includes silicon nitride (SiN), for example. The polishing adjustment material 23M is filled into the grooves G1 from the surface of the semiconductor substrate 21W.

Subsequently, as illustrated in FIG. 9D, the polishing adjustment material 23M provided on the surface of the semiconductor substrate 21W is removed by using, for example, a wet etching method. This forms the polishing adjustment section 23 embedded in the semiconductor substrate 21W. Next, the memory circuit is formed in each region surrounded by the polishing adjustment section 23 in the semiconductor substrate 21W.

Next, as illustrated in FIGS. 9E and 9F, the wiring layer 22 is formed on the semiconductor substrate 21W (FIG. 9E) and thereafter, the wiring layer 22 and the semiconductor substrate 21W are cut along lines DL (FIG. 9F). The cutting is performed using dicing, for example. The semiconductor substrate 21W in a wafer state and the wiring layer 22 are thereby divided into pieces. Here, even if contaminants adhere to the semiconductor substrate 21W in the vicinity of the lines DL during the cutting along the lines DL, it is possible to suppress entry of the contaminants into the logic circuit (the wiring region 20A) because the polishing adjustment section 23 is provided on the periphery (the peripheral region 20B) of the memory circuit.

Subsequently, as illustrated in FIG. 9G, the semiconductor substrate 21W and the wiring layer 22 divided into pieces are bonded to a semiconductor substrate 11W in a wafer state and the wiring layer 12. The semiconductor substrate 11W and the wiring layer 12W are for forming the imaging element 1. At this time, the terminal 22a of the wiring layer 22 and the terminal 12a of the wiring layer 12 are coupled to each other by, for example, a CuCu junction (the wiring line W1). Further, in order to form the logic chip 30, a semiconductor substrate 31W in a wafer state and the wiring layer 32 are cut to be divided into pieces in a similar manner to the above. The semiconductor substrate 31W and the wiring layer 32 are also bonded to the semiconductor substrate 11W in the wafer state and the wiring layer 12. The terminal 32a of the wiring layer 32 and the terminal 12a of the wiring layer 12 are coupled to each other by, for example, a CuCu junction (the wiring line W2).

Thereafter, as illustrated in FIG. 9H, the semiconductor substrates 21W and 31W are thinned by using, for example, a CMP method. The semiconductor substrate 21 of the memory chip 20 and the semiconductor substrate 31 of the logic chip 30 are thereby formed. That is, the memory chip 20 and the logic chip 30 are formed on the semiconductor substrate 11 in wafer form. Here, in the present embodiment, local excessive polishing of the semiconductor substrates 21W and 31W is suppressed because the polishing adjustment sections 23 and 33 are provided in the semiconductor substrates 21W and 31W.

Next, the buried section 50 is formed to cover the memory chip 20 and the logic chip 30. Subsequently, the support substrate 40 is bonded to the semiconductor substrate 11W with the memory chip 20 and the logic chip 30 interposed therebetween. Then, the semiconductor substrate 11W is thinned by using, for example, a CMP method. Thereafter, the color filter 61 and the on-chip lens 62 are formed on the semiconductor substrate 11W. Lastly, the semiconductor substrate 11W in wafer form and the wiring layer 12 are cut. It is possible to complete the imaging device 1 illustrated in FIG. 1 in this manner, for example.

FIGS. 10A to 10E illustrate another example of the process of manufacturing the memory chip 20 (or the logic chip 30) in order. For example, by using this method, it is possible to form the memory chip 20 and the logic chip 30 illustrated in FIGS. 7 and 8.

First, as illustrated in FIG. 10A, the wiring layer 22 is formed on the semiconductor substrate 21W in wafer form. Next, as illustrated in FIG. 10B, a photoresist PR2 patterned into a predetermined shape is formed on the wiring layer 22. Subsequently, as illustrated in FIG. 10C, a plurality of grooves G2 is formed in the wiring layer 22 and the semiconductor substrate 21W using the photoresist PR2. The grooves G2, which are for forming the polishing adjustment section 23 of the memory chip 20, penetrate the wiring layer 22 and extend partially in the thickness direction of the semiconductor substrate 21W. Each of the plurality of grooves G2 is shaped like a frame in planar shape (see (B) of FIG. 2), for example.

After the grooves G2 are formed, as illustrated in FIG. 10D, the polishing adjustment material 23M is formed into a film on the wiring layer 22. The polishing adjustment material 23M is filled into the grooves G2 from the surface of the wiring layer 22.

Subsequently, as illustrated in FIG. 10E, the polishing adjustment material 23M provided on the surface of the wiring layer 22 is removed by using, for example, a wet etching method. This forms the polishing adjustment section 23 embedded in the wiring layer 22 and the semiconductor substrate 21W. Thereafter, it is possible to complete the imaging device 1 in a manner similar to that described above.

(Operation of Imaging Device 1)

With such an imaging device 1, signal charges (for example, electrons) are acquired in the following manner, for example. Once light has passed through the on-chip lens 62, the color filter 61, and the like and entered the imaging device 1, this light is detected (absorbed) by the PD of each pixel, and red, green, or blue color light is photoelectrically converted. Among electron-hole pairs generated in the PD, signal charges (for example, electrons) are converted into imaging signals and processed at the memory circuit of the memory chip 20 and the logic circuit of the logic chip 30.

(Workings and Effects of Imaging Device 1)

In the present embodiment, the polishing adjustment section 23 is provided in the memory chip 20, and the polishing adjustment section 33 is provided in the logic chip 30. This suppresses excessive polishing of the peripheral regions 20B and 30B during polishing of the semiconductor substrates 21W and 31W (see FIG. 9H) in the process of manufacturing the imaging device 1. The workings and the effects are described below with use of a comparative example.

FIGS. 11A and 11B illustrate a method of manufacturing an imaging device according to a comparative example in order of processes. In this method also, first, the semiconductor substrates 21W and 31W in wafer form and the wiring layers 22 and 32 are cut to be divided into pieces in a similar manner to the method of manufacturing the imaging device 1 described above, following which they are bonded to the semiconductor substrate 11W in wafer form (FIG. 11A). Next, the semiconductor substrates 21W and 31W are thinned by using, for example, a CMP method (FIG. 11B). A memory chip 120 and a logic chip 130 are thereby formed.

In the method of manufacturing the imaging device according to the comparative example, neither of the semiconductor substrates 21W and 31W is provided with a polishing adjustment section (for example, the polishing adjustment section 23 or 33 in FIG. 2 or FIG. 3). Therefore, when the semiconductor substrate 21W or 31W is thinned by using a CMP method, for example, a corner of the semiconductor substrate 21W or 31W (a corner E in FIG. 12 to be described later) is more susceptible to polishing as compared with other portions). One reason for this is that a stress of a polishing pad is exerted more greatly on the corner of the semiconductor substrate 21W or 31W than on the other portions.

FIG. 12 illustrates the logic chip 130 illustrated in FIG. 11B on an enlarged scale. As illustrated, in the method of manufacturing the imaging device according to the comparative example, the corner E of the semiconductor substrate 31W (or the semiconductor substrate 21W) is excessively polished, and it is thus difficult to form a flat surface of the semiconductor substrate 31W at the corner E. If flatness of the buried layer (see the buried layer 50 in FIG. 1) is degraded due to the corner E of the semiconductor substrate 31W, a bonding failure can occur between the support substrate (the support substrate 40 in FIG. 1) and each of the memory chip 120 and the logic chip 130.

Further, when the semiconductor substrate 21W or 31W in wafer form and the wiring layer 22 or 32 are divided into pieces, a contaminant 1M adhering to a peripheral edge of the semiconductor substrate 21W or 31W can enter the memory circuit or the logic circuit via the semiconductor substrate 21W or 31W. The entry of the contaminant degrades the characteristics of the imaging device.

In contrast, in the present embodiment, the memory chip 20 and the logic chip 30 have the polishing adjustment sections 23 and 33 in the peripheral regions 20B and 30B. The polishing adjustment sections 23 and 33 have a lower polishing rate than a polishing rate of the semiconductor substrates 21W and 31W. Accordingly, even the peripheral regions 20B and 30B, which are more susceptible to polishing, are polished at a rate similar to that of the other portions, and a flat surface is thus formed across the wiring regions 20A and 30A and the peripheral regions 20B and 30B (in particular, corners). This causes the flatness of the buried layer 50 to be higher as compared with that in the imaging device according to the comparative example described above, thus making it possible to suppress the occurrence of a bonding failure between each of the memory chip 20 and the logic chip 30 and the support substrate 40.

For example, when the semiconductor substrates 21W and 31W in wafer form and the wiring layers 22 and 32 are divided into pieces (FIG. 9F), contaminants can adhere to the peripheral edges (in the vicinity of the lines DL) of the semiconductor substrates 21W and 31W. However, in the imaging device 1, the polishing adjustment sections 23 and 33 suppress entry of the contaminants into the memory circuit and the logic circuit (the wiring regions 20A and 30A). In particular, forming the polishing adjustment sections 23 and 33 using silicon nitride (SiN) makes it possible to suppress the entry of contaminants effectively. With the imaging device 1, it is thus possible to suppress degradation of characteristics caused by the contaminants.

As described above, in the present embodiment, the polishing adjustment sections 23 and 33 are provided in the memory chip 20 and the logic chip 30. This makes it possible to suppress local excessive polishing of the semiconductor substrates 21W and 31W in the process of manufacturing the imaging device 1. Accordingly, it is possible to suppress the occurrence of a defect during manufacture.

Application Example

The imaging device 1 described above is applicable, for example, to various types of electronic apparatuses such as a camera. FIG. 13 illustrates a schematic configuration of an electronic apparatus 5 (a camera) as an example thereof. The electronic apparatus 5 is, for example, a camera that is able to shoot a still image or a moving image. The electronic apparatus 5 includes the imaging device 1, an optical system (an optical lens) 310, a shutter device 311, a driver 313 that drives the imaging device 1 and the shutter device 311, and a signal processor 312.

The optical system 310 guides image light (incident light) from a subject to the imaging device 1. The optical system 310 may include a plurality of optical lenses. The shutter device 311 controls a period during which the imaging device 1 is to be irradiated with light and a period during which the light is to be blocked. The driver 313 controls a transfer operation of the imaging device 1 and a shutter operation of the shutter device 311. The signal processor 312 performs various kinds of signal processing on a signal outputted from the imaging device 1. An image signal Dout having been subjected to the signal processing is stored in a storage medium such as a memory or outputted to a monitor or the like.

<Example of Practical Application to In-Vivo Information Acquisition System>

Further, the technology according to the present disclosure (present technology) is applicable to various products. For example, the technology according to the present disclosure may be applied to an endoscopic surgery system.

FIG. 14 is a block diagram depicting an example of a schematic configuration of an in-vivo information acquisition system of a patient using a capsule type endoscope, to which the technology according to an embodiment of the present disclosure (present technology) can be applied.

The in-vivo information acquisition system 10001 includes a capsule type endoscope 10100 and an external controlling apparatus 10200.

The capsule type endoscope 10100 is swallowed by a patient at the time of inspection. The capsule type endoscope 10100 has an image pickup function and a wireless communication function and successively picks up an image of the inside of an organ such as the stomach or an intestine (hereinafter referred to as in-vivo image) at predetermined intervals while it moves inside of the organ by peristaltic motion for a period of time until it is naturally discharged from the patient. Then, the capsule type endoscope 10100 successively transmits information of the in-vivo image to the external controlling apparatus 10200 outside the body by wireless transmission.

The external controlling apparatus 10200 integrally controls operation of the in-vivo information acquisition system 10001. Further, the external controlling apparatus 10200 receives information of an in-vivo image transmitted thereto from the capsule type endoscope 10100 and generates image data for displaying the in-vivo image on a display apparatus (not depicted) on the basis of the received information of the in-vivo image.

In the in-vivo information acquisition system 10001, an in-vivo image imaged a state of the inside of the body of a patient can be acquired at any time in this manner for a period of time until the capsule type endoscope 10100 is discharged after it is swallowed.

A configuration and functions of the capsule type endoscope 10100 and the external controlling apparatus 10200 are described in more detail below.

The capsule type endoscope 10100 includes a housing 10101 of the capsule type, in which a light source unit 10111, an image pickup unit 10112, an image processing unit 10113, a wireless communication unit 10114, a power feeding unit 10115, a power supply unit 10116 and a control unit 10117 are accommodated.

The light source unit 10111 includes a light source such as, for example, a light emitting diode (LED) and irradiates light on an image pickup field-of-view of the image pickup unit 10112.

The image pickup unit 10112 includes an image pickup element and an optical system including a plurality of lenses provided at a preceding stage to the image pickup element. Reflected light (hereinafter referred to as observation light) of light irradiated on a body tissue which is an observation target is condensed by the optical system and introduced into the image pickup element. In the image pickup unit 10112, the incident observation light is photoelectrically converted by the image pickup element, by which an image signal corresponding to the observation light is generated. The image signal generated by the image pickup unit 10112 is provided to the image processing unit 10113.

The image processing unit 10113 includes a processor such as a central processing unit (CPU) or a graphics processing unit (GPU) and performs various signal processes for an image signal generated by the image pickup unit 10112. The image processing unit 10113 provides the image signal for which the signal processes have been performed thereby as RAW data to the wireless communication unit 10114.

The wireless communication unit 10114 performs a predetermined process such as a modulation process for the image signal for which the signal processes have been performed by the image processing unit 10113 and transmits the resulting image signal to the external controlling apparatus 10200 through an antenna 10114A. Further, the wireless communication unit 10114 receives a control signal relating to driving control of the capsule type endoscope 10100 from the external controlling apparatus 10200 through the antenna 10114A. The wireless communication unit 10114 provides the control signal received from the external controlling apparatus 10200 to the control unit 10117.

The power feeding unit 10115 includes an antenna coil for power reception, a power regeneration circuit for regenerating electric power from current generated in the antenna coil, a voltage booster circuit and so forth. The power feeding unit 10115 generates electric power using the principle of non-contact charging.

The power supply unit 10116 includes a secondary battery and stores electric power generated by the power feeding unit 10115. In FIG. 14, in order to avoid complicated illustration, an arrow mark indicative of a supply destination of electric power from the power supply unit 10116 and so forth are omitted. However, electric power stored in the power supply unit 10116 is supplied to and can be used to drive the light source unit 10111, the image pickup unit 10112, the image processing unit 10113, the wireless communication unit 10114 and the control unit 10117.

The control unit 10117 includes a processor such as a CPU and suitably controls driving of the light source unit 10111, the image pickup unit 10112, the image processing unit 10113, the wireless communication unit 10114 and the power feeding unit 10115 in accordance with a control signal transmitted thereto from the external controlling apparatus 10200.

The external controlling apparatus 10200 includes a processor such as a CPU or a GPU, a microcomputer, a control board or the like in which a processor and a storage element such as a memory are mixedly incorporated. The external controlling apparatus 10200 transmits a control signal to the control unit 10117 of the capsule type endoscope 10100 through an antenna 10200A to control operation of the capsule type endoscope 10100. In the capsule type endoscope 10100, an irradiation condition of light upon an observation target of the light source unit 10111 can be changed, for example, in accordance with a control signal from the external controlling apparatus 10200. Further, an image pickup condition (for example, a frame rate, an exposure value or the like of the image pickup unit 10112) can be changed in accordance with a control signal from the external controlling apparatus 10200. Further, the substance of processing by the image processing unit 10113 or a condition for transmitting an image signal from the wireless communication unit 10114 (for example, a transmission interval, a transmission image number or the like) may be changed in accordance with a control signal from the external controlling apparatus 10200.

Further, the external controlling apparatus 10200 performs various image processes for an image signal transmitted thereto from the capsule type endoscope 10100 to generate image data for displaying a picked up in-vivo image on the display apparatus. As the image processes, various signal processes can be performed such as, for example, a development process (demosaic process), an image quality improving process (bandwidth enhancement process, a super-resolution process, a noise reduction (NR) process and/or image stabilization process) and/or an enlargement process (electronic zooming process). The external controlling apparatus 10200 controls driving of the display apparatus to cause the display apparatus to display a picked up in-vivo image on the basis of generated image data. Alternatively, the external controlling apparatus 10200 may also control a recording apparatus (not depicted) to record generated image data or control a printing apparatus (not depicted) to output generated image data by printing.

The description has been given above of one example of the in-vivo information acquisition system to which the technology according to the present disclosure is applicable. The technology according to the present disclosure is applicable to, for example, the image pickup unit 10112 among the configurations described above. This makes it possible to improve accuracy of detection.

<Example of Practical Application to Endoscopic Surgery System>

The technology according to the present disclosure (present technology) is applicable to various products. For example, the technology according to the present disclosure may be applied to an endoscopic surgery system.

FIG. 15 is a view depicting an example of a schematic configuration of an endoscopic surgery system to which the technology according to an embodiment of the present disclosure (present technology) can be applied.

In FIG. 15, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

FIG. 16 is a block diagram depicting an example of a functional configuration of the camera head 11102 and the CCU 11201 depicted in FIG. 15.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

The description has been given above of one example of the endoscopic surgery system to which the technology according to the present disclosure is applicable. The technology according to the present disclosure is applicable to, for example, the image pickup unit 11402 among the configurations described above. Applying the technology according to the present disclosure to the image pickup unit 11402 makes it possible to improve accuracy of detection.

It is to be noted that although the endoscopic surgery system has been described as an example here, the technology according to the present disclosure may also be applied to, for example, a microscopic surgery system, and the like.

<Example of Practical Application to Mobile Body>

The technology according to the present disclosure is applicable to various products. For example, the technology according to the present disclosure may be achieved as a device mounted on any type of mobile body such as a vehicle, an electric vehicle, a hybrid electric vehicle, a motorcycle, a bicycle, a personal mobility, an airplane, a drone, a vessel, a robot, a construction machine, or an agricultural machine (tractor).

FIG. 17 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 17, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 17, an audio speaker 12061, a display section 12062, and an instrument panel 12063 are illustrated as the output device. The display section 12062 may, for example, include at least one of an on-board display and a head-up display.

FIG. 18 is a diagram depicting an example of the installation position of the imaging section 12031.

In FIG. 18, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 18 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

The description has been given above of one example of the vehicle control system to which the technology according to the present disclosure is applicable. The technology according to the present disclosure is applicable to, for example, the imaging section 12031 among the configurations described above. Applying the technology according to the present disclosure to the imaging section 12031 makes it possible to obtain a captured image that is easier to see. Hence, it is possible to reduce fatigue of the driver.

The description has been given with reference to the embodiment; however, the contents of the present disclosure are not limited to the above-described embodiment, and may be modified in a variety of ways. For example, the configuration of the imaging device described in the embodiment above is merely exemplary, and may further include any other layer. In addition, the material and thickness of each layer are merely exemplary as well, and are not limited to those described above.

Further, in the embodiment above, description has been given of an example where the imaging device 1 includes the imaging element 10, the memory chip 20, and the logic chip 30; however, it is sufficient that the imaging device 1 includes at least two semiconductor chips. Further, the imaging device 1 may include four or more semiconductor chips.

Further, in the embodiment above, description has been given of a case where the CuCu junction is used to couple the memory chip 20 and the imaging element 10 to each other, and to couple the logic chip 30 and the imaging element 10 to each other; however, they may be coupled using any other method. For example, they may be coupled using a rewiring layer, or alternatively, they may be electrically coupled by any other method such as a through electrode.

Further, in the embodiment above, description has been given of a case where the polishing adjustment sections (the polishing adjustment sections 23 and 33) are provided in both of the memory chip 20 and the logic chip 30; however, a polishing adjustment section may be provided in one of the memory chip 20 and the logic chip 30.

Further, in the embodiment above, description has been given of a case where the memory chip 20 and the logic chip 30 are coupled to the imaging element 10; however, any chip to be coupled to the imaging element 10 may have any other configuration.

It is to be noted that the effects described in the embodiment and the like above are merely exemplary, and may be any other effects or may further include any other effects.

It is to be noted that the present disclosure may have the following configurations. According to the imaging device having the following configurations, the provision of the polishing adjustment section in the semiconductor element makes it possible to suppress local excessive polishing of the semiconductor substrate in the process of manufacturing the imaging device. Accordingly, it is possible to suppress the occurrence of a defect during manufacture.

(1)
An imaging device including
an imaging element, and a semiconductor element provided to be opposed to the imaging element and electrically coupled to the imaging element, in which
the semiconductor element includes:
a wiring region provided in a middle portion and a peripheral region outside the wiring region;
a wiring layer having a wiring line in the wiring region;
a semiconductor substrate opposed to the imaging element with the wiring layer interposed therebetween and having a first surface and a second surface in order from a side of the wiring layer; and
a polishing adjustment section including a material that is lower in polishing rate than a constituent material of the semiconductor substrate, the polishing adjustment section being disposed in at least a portion of the peripheral region and provided in a thickness direction of the semiconductor substrate from the second surface.

(2)
The imaging device according to (1), in which
a planar shape of the semiconductor substrate includes a corner, and
the polishing adjustment section is provided at least at the corner.

(3)
The imaging device according to (1) or (2), in which the polishing adjustment section is provided to surround the wiring region.

(4)
The imaging device according to (1) or (2), in which a plurality of the polishing adjustment sections are disposed to be separated from each other around the wiring region.

(5)
The imaging device according to any one of (1) to (4), in which the polishing adjustment section includes
a first polishing adjustment section, and
a second polishing adjustment section disposed at a position farther from the wiring region than the first polishing adjustment section.

(6)
The imaging device according to any one of (1) to (5), in which the polishing adjustment section is provided in the semiconductor substrate and the wiring layer.

(7)
The imaging device according to any one of (1) to (6), further including a support substrate opposed to the imaging element with the semiconductor element interposed therebetween.

(8)
The imaging device according to (7), further including, between the support substrate and the imaging element, a buried layer surrounding the semiconductor element.

(9)
The imaging device according to any one of (1) to (8), including a plurality of the semiconductor elements.

(10)
The imaging device according to any one of (1) to (9), in which the polishing adjustment section includes silicon nitride or silicon oxide.

This application claims priority from Japanese Patent Application No. 2018-202769 filed on Oct. 29, 2018 with the Japan Patent Office, the entire contents of which are incorporated in the present application by reference.

It should be understood by those skilled in the art that various modifications, combinations, sub-combinations and alterations may occur depending on design requirements and other factors insofar as they are within the scope of the appended claims or the equivalents thereof.

The invention claimed is:

1. An imaging device comprising
an imaging element, and a semiconductor element provided to be opposed to the imaging element and electrically coupled to the imaging element, wherein
the semiconductor element includes:
a wiring region provided in a middle portion and a peripheral region outside the wiring region;
a wiring layer having a wiring line in the wiring region;
a semiconductor substrate opposed to the imaging element with the wiring layer interposed therebetween and having a first surface and a second surface in order from a side of the wiring layer; and
a polishing adjustment section including a material that is lower in polishing rate than a constituent material of the semiconductor substrate, the polishing adjustment section being disposed in at least a portion of the peripheral region and provided in a thickness direction of the semiconductor substrate from the second surface.

2. The imaging device according to claim 1, wherein
a planar shape of the semiconductor substrate includes a corner, and
the polishing adjustment section is provided at least at the corner.

3. The imaging device according to claim 1, wherein the polishing adjustment section is provided to surround the wiring region.

4. The imaging device according to claim 1, wherein a plurality of the polishing adjustment sections are disposed to be separated from each other around the wiring region.

5. The imaging device according to claim 1, wherein the polishing adjustment section includes
a first polishing adjustment section, and
a second polishing adjustment section disposed at a position farther from the wiring region than the first polishing adjustment section.

6. The imaging device according to claim 1, wherein the polishing adjustment section is provided in the semiconductor substrate and the wiring layer.

7. The imaging device according to claim 1, further comprising a support substrate opposed to the imaging element with the semiconductor element interposed therebetween.

8. The imaging device according to claim 7, further comprising, between the support substrate and the imaging element, a buried layer surrounding the semiconductor element.

9. The imaging device according to claim 1, comprising a plurality of the semiconductor elements.

10. The imaging device according to claim 1, wherein the polishing adjustment section includes silicon nitride or silicon oxide.

* * * * *